US008085165B2

(12) United States Patent  
Wavering et al.

(10) Patent No.: US 8,085,165 B2
(45) Date of Patent: Dec. 27, 2011

(54) WIRELESS CORROSION SENSOR

(75) Inventors: Thomas A. Wavering, Charlottesville, VA (US); Fritz J. Friedersdorf, Earlysville, VA (US); Charles L. Bopp, III, Long Beach, CA (US)

(73) Assignee: Luna Innovations Incorporated, Roanoke, VA (US)

( * ) Notice: Subject to any disclaimer, the term of this patent is extended or adjusted under 35 U.S.C. 154(b) by 994 days.

(21) Appl. No.: 12/027,850

(22) Filed: Feb. 7, 2008

(65) Prior Publication Data

US 2008/0204275 A1 Aug. 28, 2008

Related U.S. Application Data

(60) Provisional application No. 60/900,332, filed on Feb. 9, 2007.

(51) Int. Cl.
*G08C 23/00* (2006.01)
(52) U.S. Cl. .................................. 340/870.02
(58) Field of Classification Search ........... 340/870.01, 340/870.16, 870.31–870.36
See application file for complete search history.

(56) References Cited

U.S. PATENT DOCUMENTS

| | | | |
|---|---|---|---|
| 4,019,133 A * | 4/1977 | Manley et al. ............ | 324/700 |
| 4,146,834 A * | 3/1979 | Maltby et al. ............ | 324/610 |
| 4,280,124 A * | 7/1981 | Wuertele .................. | 340/650 |
| 4,295,092 A | 10/1981 | Okamura | |
| 4,380,763 A | 4/1983 | Peart et al. | |
| 4,426,618 A | 1/1984 | Ronchetti et al. | |
| 4,755,744 A | 7/1988 | Moore et al. | |
| 4,780,664 A | 10/1988 | Ansuini et al. | |
| 4,806,849 A | 2/1989 | Kihira et al. | |
| 4,839,580 A | 6/1989 | Moore et al. | |
| 4,994,159 A | 2/1991 | Agarwala et al. | |
| 5,221,893 A | 6/1993 | Kondou et al. | |
| 5,243,297 A | 9/1993 | Perkins et al. | |

(Continued)

FOREIGN PATENT DOCUMENTS

JP 2005069883 * 3/2005

(Continued)

OTHER PUBLICATIONS

Gerhardus et al., Corrosion Costs and Preventive Strategies in the United States, 2001, Technologies Laboratories, Inc. to Federal Highway Administration (FHWA), Office of Infrastructure Research and Development, Report FHWA-RD-01-156.

(Continued)

*Primary Examiner* — Albert W Paladini
(74) *Attorney, Agent, or Firm* — Nixon & Vanderhye P.C.

(57) ABSTRACT

A passive sensor that is located on or adjacent to a structure that can be used to monitor the affect of environment on a structure or coating that is used to protect the structure. The sensor includes a parasitic element that interacts with the environment and influences the intensity of the electromagnetic response between the inductive element of the sensor and the antenna of the interrogation reader device. The condition of the parasitic element is determined by the radio frequency interaction of the reader antenna and the inductive element of the sensor. The parasitic element condition correlates to the environmental severity, or corrosivity of the environment and damage to metallic structures or protective coatings. An integrated circuit within the sensor is capable of storing identification, time, material, and measurement information. The sensor and system of the present invention is useful for tracking and monitoring cumulate environmental damage to a structure.

18 Claims, 17 Drawing Sheets

U.S. PATENT DOCUMENTS

| | | |
|---|---|---|
| 5,286,357 A | 2/1994 | Smart et al. |
| 5,310,470 A | 5/1994 | Agarwala et al. |
| 5,338,432 A | 8/1994 | Agarwala et al. |
| 5,367,583 A | 11/1994 | Sirkis |
| 5,583,426 A | 12/1996 | Tiefnig |
| 5,627,749 A | 5/1997 | Waterman et al. |
| 5,792,337 A | 8/1998 | Padovani et al. |
| 5,854,557 A | 12/1998 | Tiefnig |
| 5,942,991 A | 8/1999 | Gaudreau et al. |
| 5,977,782 A | 11/1999 | Kordecki |
| 6,054,038 A | 4/2000 | Davis et al. |
| 6,144,026 A | 11/2000 | Udd et al. |
| 6,313,646 B1 | 11/2001 | Davis et al. |
| 6,328,878 B1 | 12/2001 | Davis et al. |
| 6,490,927 B2 | 12/2002 | Braunling et al. |
| 6,564,620 B1 | 5/2003 | Jaeger |
| 6,796,187 B2 | 9/2004 | Srinivasan et al. |
| 6,919,729 B2 | 7/2005 | Tiefnig |
| 6,965,708 B2 | 11/2005 | Luo et al. |
| 7,034,660 B2 | 4/2006 | Watters et al. |
| 7,086,593 B2 | 8/2006 | Woodard et al. |
| 7,129,471 B2 * | 10/2006 | Frot et al. .................. 250/227.14 |
| 7,145,453 B2 | 12/2006 | Miller, Jr. et al. |
| 7,313,947 B2 | 1/2008 | Harris et al. |
| 2006/0125493 A1 | 6/2006 | Subramanian et al. |
| 2007/0120572 A1 | 5/2007 | Chen et al. |
| 2007/0241762 A1 | 10/2007 | Varpula et al. |
| 2007/0282541 A1 | 12/2007 | Griess et al. |

FOREIGN PATENT DOCUMENTS

| | | |
|---|---|---|
| WO | WO 2007/108890 | 9/2007 |

OTHER PUBLICATIONS

ASTM G1-03 Standard Practice for Preparing, cleaning, and Evaluating Corrosion Test Specimens, 2003, ASTM International: West Conshocken, PA.

Related U.S. Appl. No. 11/276,805, filed Mar. 15, 2006; Inventor: Baude et al.

* cited by examiner

WIRELESS CORROSION SENSOR

RELATED APPLICATION

This application claims priority from U.S. Provisional patent application 60/900,332, filed on Feb. 9, 2007, which is incorporated herein by reference in its entirety.

STATEMENT REGARDING FEDERALLY SPONSORED RESEARCH OR DEVELOPMENT

Work relating to this application was performed under U.S. Army Research Laboratory Contract No. 911QX-06-C-0076.

TECHNICAL FIELD

The technical field relates to wireless corrosion sensors, material degradation sensors, condition sensors, wireless, electrical, and chemical sensors, dielectric property measurement, antenna design, and electrical circuits.

BACKGROUND

Corrosion has a significant impact on the performance and reliability of U.S. infrastructure, transportation, utilities, production and manufacturing. Gerhardus reports that the total direct cost of corrosion to the U.S. has been estimated to be $279 billion per year, which is 3.2 percent of the U.S. gross domestic product. Critical needs have been identified for new technologies or corrosion management techniques including advance monitoring and detection systems for corrosion management, life prediction and performance assessment.

Numerous engineering materials in common use are degraded through corrosion processes. For example, metals and alloys such as steel and aluminum often corrode when exposed to industrial or marine atmospheric environments. Such corrosion processes often cause damage to equipment and structures fabricated from these materials, leading to reduced operational life and reliability. To minimize the undesirable consequences of corrosion on product usability, reliability, and lifetime, it is often desirable to repair or maintain corroded materials before they reach a critical level of damage. For example, some portions of vehicles are more prone to corrosion than others; the bottom of vehicles often has more corrosion than the top. In this case, it is desirable to repair or repaint the areas along the bottom and underside before they degrade to the point that the vehicle function and/or reliability is adversely affected.

Low cost and easy to use corrosivity sensors are required to manage corrosion and reduce life cycle costs, improve performance, and minimize corrosion related failures. Knowledge of cumulative environmental severity, corrosion damage accumulation, and corrosion protection system breakdown would enable more effective prediction and management of asset life, performance and maintenance. The corrosion monitoring system would provide field performance data on new coatings and paint systems and would be a means for determining the effectiveness and return on investment of corrosion prevention and control programs. The requirements for a corrosion monitoring system to be successful are: low cost, small size and weight, wide deployment capability, easy installation, simple operation and data analysis and low maintenance.

Various measuring methods may be used to detect and monitor corrosion. One of the most basic methods requires placement, exposure, and retrieval of mass loss coupons. Another class of sensors requires direct connection to the sensing device including electrical, fiber optic and possibly acoustic devices that may measure either material loss, corrosion rate or environmental parameters that promote corrosion. An automated variant of mass loss coupon measurements is the electrical resistance probe. Electrochemical measurement techniques include electrochemical impedance spectroscopy, electrochemical noise, galvanic currents, redox potential, and linear polarization resistance methods. Similarly, chemical and environmental sensing devices may measure temperature, ion concentration, pH, dissolved oxygen, moisture, etc.

Electrical and fiber optic sensor techniques and apparatus require direct connection to the sensor, and therefore, require that the reader used to determine the state of the sensor be placed in direct physical contact with the sensing element. This requires the use of wires or fiber running from the corrosion sensor to a powered reader device. The need for a direct electrical or physical contact is a serious drawback, as it limits the placement of sensors to regions where wire can be routed or direct connection can be made. In addition, the process of making these connections and associated measurements is difficult and time consuming. To overcome these limitations systems have been developed that contain power, processors and wireless transceivers that can be located near or with the sensing element. This increases system complexity requires dedicated communication and processor hardware for each sensing element and sensor power. These actively powered devices may have limited service lives and require maintenance such as battery replacement.

A basic corrosivity measurement technique uses mass loss samples that are placed in the environment of interest. This technique is detailed in ASTM G1-03 Standard Practice for Preparing, Cleaning, and Evaluating Corrosion Test Specimens. This technique is simple and reliable, but requires that the samples be retrieved periodically for cleaning and mass loss measurements. Also, the accuracy of the measurement depends on the mass of the sample and the total amount of material removed by corrosion. Accurate measurements may require very long exposure times of months to years. The long sampling intervals, need for sample racks, and laboratory measurement of weight loss all restrict the use and limit the value of this measurement technique.

Electrochemical sensor measurements include electrochemical potential, linear polarization resistance, electrochemical impedance spectroscopy, electrochemical noise measurements, and galvanic current measurements. These techniques all measure the instantaneous conditions of electrodes to determine corrosion conditions or corrosion rates. These methods are highly dependent on the conductivity of the surrounding environment and will not measure corrosion in the absence of a conductive medium. A significant disadvantage of these techniques is the lack of a direct measure of cumulative corrosion damage. Indirect measurement of total corrosion can be obtained only through a continuous monitoring of the corrosion rate. This requires dedicated data collection and processing hardware and software.

Measurements of environmental conditions or chemistry such as temperature, pH, time of wetness, relative humidity, and ion concentrations have been used by Srinivasan U.S. Pat. No. 6,796,187 and Watters U.S. Pat. No. 7,034,660 to infer corrosivity of a given environment. These are indirect methods that depend on empirical equations to estimate corrosion and do not measure the cumulative corrosion damage or corrosion rate. As with electrochemical measurements, these are instantaneous condition measurements, and the only way to infer cumulative environmental corrosivity and predict total corrosion is to continuous collect and record data that can then be used in models that predict damage state based on environmental parameters.

The electrical resistance technique is another method for corrosion measurement. This measurement is based on the change of resistance of a sensing element as it corrodes or is otherwise damaged by the environment. The change, e.g., diminution of size of the object, increases the resistance of the metallic specimen and, therefore, directly relates to the loss of metal by corrosion and/or erosion. The data can be converted to unit loss of metal per time unit to provide corrosion rate per year or similar time period. The resistance measurement requires the direct connection of an ohmmeter or some equivalent measurement device to the sensor. The measurement range and sensitivity is dependent on the length and cross sectional area of the sensing element. In general, long thin patterns of metallic conductors are used to achieve the desired service life and desired damage sensitivity. Changes in resistance of the specimens due to diminution of mass are small, and range within milli and micro-ohms. As such, signals with sufficient noise levels are difficult to obtain and readily subject to extraneous influences. Should the sensing element be perforated and the conductive path interrupted the sensor will not function. These sensors have poor resolution during the initial stages of corrosion, and to obtain reasonable service life, the corrosion needs to be a uniform general attack, not localized.

Other measurement methods by Tiefnig U.S. Pat. No. 6,919,729 are described that use changes in inductance of a current carrying coil to measure corrosion damage. In these techniques, a coil contains or is in proximity of a mass of metal that is the sensing element. As the metal is removed by corrosion the inductance of the coil changes and this can be used as a measure of corrosion damage. The technique requires direct connection of the coil to a power source to make the measurement. The need for this direct connection is a disadvantage for use under coatings or in situations where leads are inconvenient such as on the exterior of a vehicle, or where leads and connections may also be damaged or corroded.

A variety of wireless devices powered externally are described in the literature. A number of these methods require that the sensor be interrogated to determine the resonant frequency or Q factor using an external device reader. These methods involve sensing elements within the circuit that when altered by the physical affect to be monitoring the resonant frequency of the circuit is modified. This method constrains the sensor design to structures that produce changes in the resonant frequency as a function of corrosion damage, must have provisions for determining the resonant frequency with a wireless reader, and have the sensing element electrically connected to an electrical circuit.

The wireless device of Varpula US 2007/0241762 for monitoring environmental conditions using an inductive element that is not electrically (galvanically) connected to the resonant circuit requires determination of the resonant frequency or quality (Q) factor for detecting environmental contaminants. It also does not provide for reference measurements, correlation to structural conditions, identification and data storage, or operation on metal substrates.

Woodard U.S. Pat. No. 7,086,593 discloses a resonant electrical circuit that senses physical changes in the environment by changes in the capacitive element of the electrical circuit. Changes in the capacitive element of the circuit alter the resonant frequency of the circuit. The sensing element is formed from metal conductors that have parallel plates or interdigitated printed pattern geometries. The capacitance change is dependent on environmental interaction with the dielectric medium between the two capacitor electrodes. This device does not directly sense corrosion and is therefore only capable of monitoring conditions that may cause corrosion. Also, without continuous monitoring, no historical measure of cumulative damage is possible.

Another device by Subramanian US 2006/0125493 discloses the use of a coil wirelessly coupled to an antenna that can be used to power a corrosion sensor. The resistance of the sensing element is a function of the corrosion damage and this property change is used to measure corrosion damage. As with traditional resistance sensors, the measurement range and sensitivity is dependent on the length and cross sectional area of the sensing element. In general, long thin patterns of metallic conductors are used to achieve the desired service life and desired damage sensitivity. Should the sensing element be perforated and the conductive path be interrupted the sensor will not function. These sensors have poor resolution during the initial stages of corrosion and to obtain reasonable service life the corrosion needs to be a uniform general attack, not localized.

The above methods for monitoring corrosion by wireless sensing devices have several disadvantages. These methods do not include a reference sensor in the sensor design. Without a reference sensor, it is difficult to quantify the amount of environmental damage seen by the sensor. Each measurement of the sensor requires controlling every variable that influences the response of the sensor to interrogation including distance between the sensor and interrogator, polarization of the sensor relative to the interrogator, and environmental factors not being sensed by the sensor. The methods based on resonant frequency response require many measurements to be taken over a wide range of frequencies. Taking and analyzing this data is computationally intense and time consuming. Finally, methods for treating the case when the monitored structure is a conductor is not described.

Sirkis U.S. Pat. No. 5,367,583 discloses the characterization of corrosion using optical sensing techniques. The corrosion sensor acts as a mirror in a Fabry-Perot cavity; corrosion-induced changes in reflectance are measured optically to determine the extent of corrosion. Udd U.S. Pat. No. 6,144,026 discloses an optical corrosion characterization technique. Corrosion sensor systems are formed by using one or more fiber gratings whose transverse strains vary with corrosion or chemical attack. By optical probing, it is therefore possible to determine the corrosion along the fiber. Optical techniques require that the sensor be physically connected to the interrogation hardware. These measurements provide only limited information on material loss and corrosion rate and are computationally intensive to convert the optical signal to corrosion damage. The need for direct connection precludes the use of this device under coatings or in harsh environments where the connectors can be fouled or damaged.

In view of the many drawbacks associated with corrosion sensing devices and techniques, there is a need for a corrosivity sensor and monitoring system where the output correlates to cumulative exposure and damage accumulation of a component, vehicle or structure, that is simple in design and operation, easy to read, does not require direct electrical contact to the sensing element, and can be used on metal structures.

SUMMARY

The above problems and needs are solved using a passive sensor that can be interrogated using a wireless reader to monitor the cumulative corrosion damage or degradation. A diagnostic corrosion monitoring system is provided that is capable of monitoring cumulative environmental severity and environmental damage to metals and coated metal components, vehicles and structures. The corrosivity monitoring system provides information on corrosion and environment induced damage that may be used for applications such as individual structure maintenance, performance metrics, obtaining field data on coating systems, and for tracking results of corrosion prevention and control activities. The diagnostic information will improve maintenance and repair practices for managing corrosion of vehicles and structures.

A sensor is provided for sensing an affect of an environment on a structure on or near which the sensor is located. The sensor includes a substrate, an inductive element formed on a substrate for receiving electromagnetic radiation with a particular electromagnetic response, a protective film that isolates the inductive element from the environment, and a parasitic element proximate to the inductive element and having a first affect on the electromagnetic response. As the environment interacts with and changes at least one characteristic of the parasitic element, the changed parasitic element has a second, different affect on the electromagnetic response of the inductive element that is detectable by a sensor reader. By monitoring the second affect as a function of time, the affect of the environment on the characteristic of the parasitic element can be determined along with the expected environmentally-induced changes to the condition of the structure.

The change to the structure includes one or more of: corrosion, erosion, exposure, physical or chemical change, a cumulative damage, or degradation of the structure or a protective coating on the structure. The parasitic element may be any geometry within, covering, or outside the inductive element that is in close proximity to but electrically insulated from the inductive element.

The sensor also includes an integrated circuit connected to the inductive element enabling storage and communication of sensor information including, but not limited to, identification, date/time stamp, material description, or prior sensor measurements. The integrated circuit is wirelessly powered by electromagnetic radiation received from the sensor reader via the inductive element. A material such as an electromagnetic absorber may be provided between the sensor and the structure for operation on metallic structures. A coating may also be provided on the parasitic element for monitoring a condition of a coating on the structure.

In addition to the sensor, a sensing system also includes a sensor reader including one or more antennas, a transmitter, connected to one or more antennas, for transmitting electromagnetic radiation that interacts with the sensor, a receiver, connected to the one or more antennas, for detecting an amount of electromagnetic radiation provided by the sensor in response to the transmitted electromagnetic radiation, and a processor for determining environmentally induced change to the structure based on a change in the electromagnetic response caused by environmentally induced changes to the parasitic element.

The electromagnetic radiation between the sensor and the sensor reader can be near field electromagnetic radiation communicated wirelessly. Alternatively, the electromagnetic radiation between the sensor and the sensor reader may be far field electromagnetic radiation communicated wirelessly, wherein the sensor is configured to reflect back to the sensor reader a modulated version of the transmitted electromagnetic radiation. In different example implementation, the inductive element can be an antenna, the parasitic element can be a conductor that is in close proximity to but electrically insulated from the inductive element. The sensor may be attached to a structure and changes to the parasitic element can be correlated to an environmentally-induced change to the structure.

The reader is preferably configured to receive another amount of electromagnetic radiation provided by the reference element in response to the transmitted electromagnetic radiation. The other amount of radiation response of the reference element is substantially unaffected by the parasitic element. The processor is configured to reduce or eliminate one or more environmental factors other than the desired one or more characteristics using the reference element response.

The processor is also preferably configured to differentiate between the inductive sensor element associate with the parasitic element and the reference element based on one or more of the following: resonant frequency of the element, polarization of the element, phase of the element, differences in timing associated with the radiation received from the element, or differences in information modulated onto the radiation received from the element. The processor can differentiate between the inductive element and the reference element based on differences in information modulated onto the radiation received from the element. Moreover, the processor may quantify a amplitude of the radiation received from each of the inductive element and the reference element.

In the following, reference numerals and figures are identified only to point to non-limiting examples to aid in understanding. In FIG. 1 the corrosivity monitoring system (19) includes a corrosivity sensor (26), a reader (22) (transmitter/receiver unit), and a data processing unit (24) that supports data display (23) and storage (25). In one example embodiment as shown in FIG. 2, the corrosivity sensor (26 in FIG. 1) is composed of a parasitic sensor (30) that contains a parasitic element (31), protective film (32), and substrate (35) that carries a metal inlay inductive element (33) and integrated circuit (34). The substrate (35), inductive element (33) and integrated circuit (34) may be near field or far field RFID transponder devices (90). In FIG. 1 the reader unit (22) includes a transmitter and receiver antenna(s) (21) and circuitry, which may be combined into one transceiver that interrogates the sensor (26) wirelessly and returns information received from the sensor (26) to the data processing unit (24). The corrosivity sensor (26) is passive, having no internal power source, and is externally powered by the transmitted electromagnetic energy from the reader (22). The data processing unit (24) correlates the data received by the reader to an environmental effect on the parasitic element (31) in FIG. 2.

The corrosivity sensor (26) in FIG. 1 can sense cumulative environment affects, environmental severity or corrosivity using the parasitic element (31) within the parasitic sensor (30), both in FIG. 2. In FIG. 2 the parasitic element (31) is exposed to the environment (27) of interest, and can be corroded or eroded due to the surrounding environmental conditions. As the parasitic material is removed or corroded, the response of the parasitic sensor (30) is altered. In a preferred example embodiment, the corrosivity sensor (26) of FIG. 1 includes a reference sensor (50) of FIG. 4 that is unaffected by changes in the parasitic element (31) and can be used to compensate for uncontrolled environmental factors, other than those associated with changes to the parasitic element (31). In this way, the corrosivity sensor (26) can be used to determine total cumulative damage or corrosive attack at any point in time when interrogated with the reader (22) of the wireless measurement system (20) in FIG. 1.

In FIG. 3 the corrosivity sensing system measurement is initiated through a user interface (42), such as a graphical user interface (GUI), that triggers the reader and activates the data acquisition (DAQ) system (40). In FIG. 1 the corrosivity sensor (26) response includes acquired waveforms from the parasitic sensor (30) of FIG. 2 and, if present, the reference sensor (50) of FIG. 4. These signals contain unique RFID transponder identification information and signals that can be used to quantify degree of corrosion of the parasitic element (31). Signal processing is performed to determine the magnitude of the response from the parasitic sensor (30) used to quantify the state of parasitic element (31) of FIG. 2. Similarly, in a preferred example embodiment in FIG. 4 the magnitude of the reference sensor (50) response is used to normalize FIG. 2's parasitic sensor (30) response. In FIG. 4 as the parasitic element (31) degrades or corrodes due to the environment (27), the magnitude of the FIG. 2 parasitic sensor (30) response increases. In FIG. 1 the corrosivity data and specific transponder identification information are stored in a database (25) that is available to local and network users. The data may be displayed as a time based trend chart or provide an audible or visual alarm as to the need for inspection and maintenance of the component, structure, or vehicle. The database information is useful for tracking cumulative corrosivity and environmental severity that a component, structure or vehicle has experienced.

Multiple sensors may be used on a single structure to monitor different components, areas, aspects, and/or environmental conditions that may occur over or within a structure or vehicle. The sensors are flat, thin and flexible and do not interfere with the function of the structure being monitored. The corrosivity sensor (26) in FIG. 1 can be use in a bare uncoated condition or a coated condition. In addition to the corrosivity monitoring, the identification information contained in the integrated circuit of the RFID transponder (90), FIG. 2, can be used to track individual components or vehicles as part of an overall condition-based maintenance and asset tracking program.

Thus, a diagnostic environmental corrosion monitoring system (19) of FIG. 1 is provided that is capable of monitoring environmental severity or corrosivity. The corrosivity sensor (26) in FIG. 1 provides a quantitative measure of corrosion and environment damage to a parasitic element that can be used for applications such as structural heath monitoring, measuring coating system condition, and tracking results of corrosion prevention and control activities. The diagnostic information can be used to improve the effectiveness of maintenance and corrosion prevention and control efforts.

DETAILED DESCRIPTION

Figure 1:
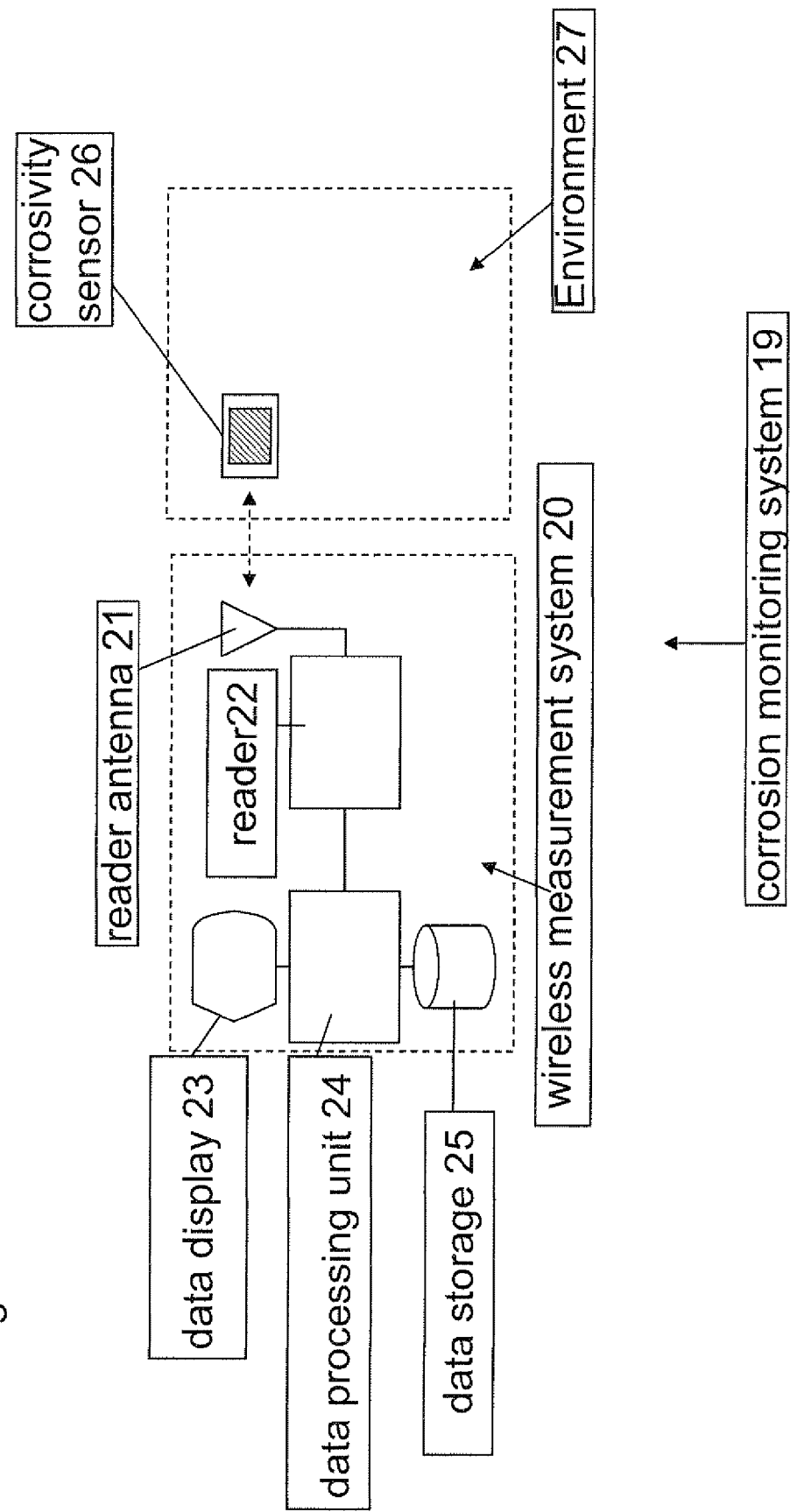
FIG. 1. Block diagram of corrosivity monitoring system.

A non-contact measurement system and method are described that is useful in measuring and monitoring the corrosive or erosive damage caused by different environments. Referring to FIG. 1, a corrosivity sensor (26) can be interrogated wirelessly, and therefore, does not require a direct electrical connection between the corrosivity sensor (26) and a reader (22) to make a measurement. The thin, flexible corrosivity sensor (26) can be applied and interrogated on dielectric (non-conductive) and conductive surfaces of components, structures and vehicles such as bridges, ships, ground vehicles and aircraft. Depending on the application, the corrosivity sensor (26) may be exposed to the environment (27) when placed on or within a structure or vehicle. The sensor may also be used to monitor or detect the breakdown of protective coatings. In this case, the corrosivity sensor (26) affixed to the surface of a structure or vehicle, can be painted with the coatings used to protect the structure. Therefore, the sensor may be useful for monitoring coating breakdown and cumulative environmental exposure. These measurements of corrosivity or coating condition can be used to anticipate damage to structural metals and alloys for the purposes of condition based maintenance and inspections.

The corrosivity sensing system (19) in FIG. 1 includes the corrosivity sensor (26), the reader (22) (transmitter receiver unit), and a data processing unit (24). The reader unit includes a transmitter and receiver antenna(s) (21), which may be combined into one transceiver that interrogates the sensor wirelessly and returns information received from the sensor to the data processing unit (24). The corrosivity sensor (26) is passive and designed such that it can sense cumulative environmental damage to the parasitic element (31) in FIG. 2 due to corrosion or other processes that remove material from the parasitic element (31). The corrosivity sensor (26) returns this information to the reader (22) when interrogated. The only power source for the sensors is derived from the transmitted electromagnetic energy of the reader (22). The data processing unit (24) correlates the data received by the reader (22) to a corrosivity damage state of the parasitic element (31). Multiple sensors may be distributed on a single structure or over multiple structures to monitor the range of environmental damage that may occur. The sensors are flexible and thin so they can be conformed and adhered to the structure to be monitored.

Figure 2:
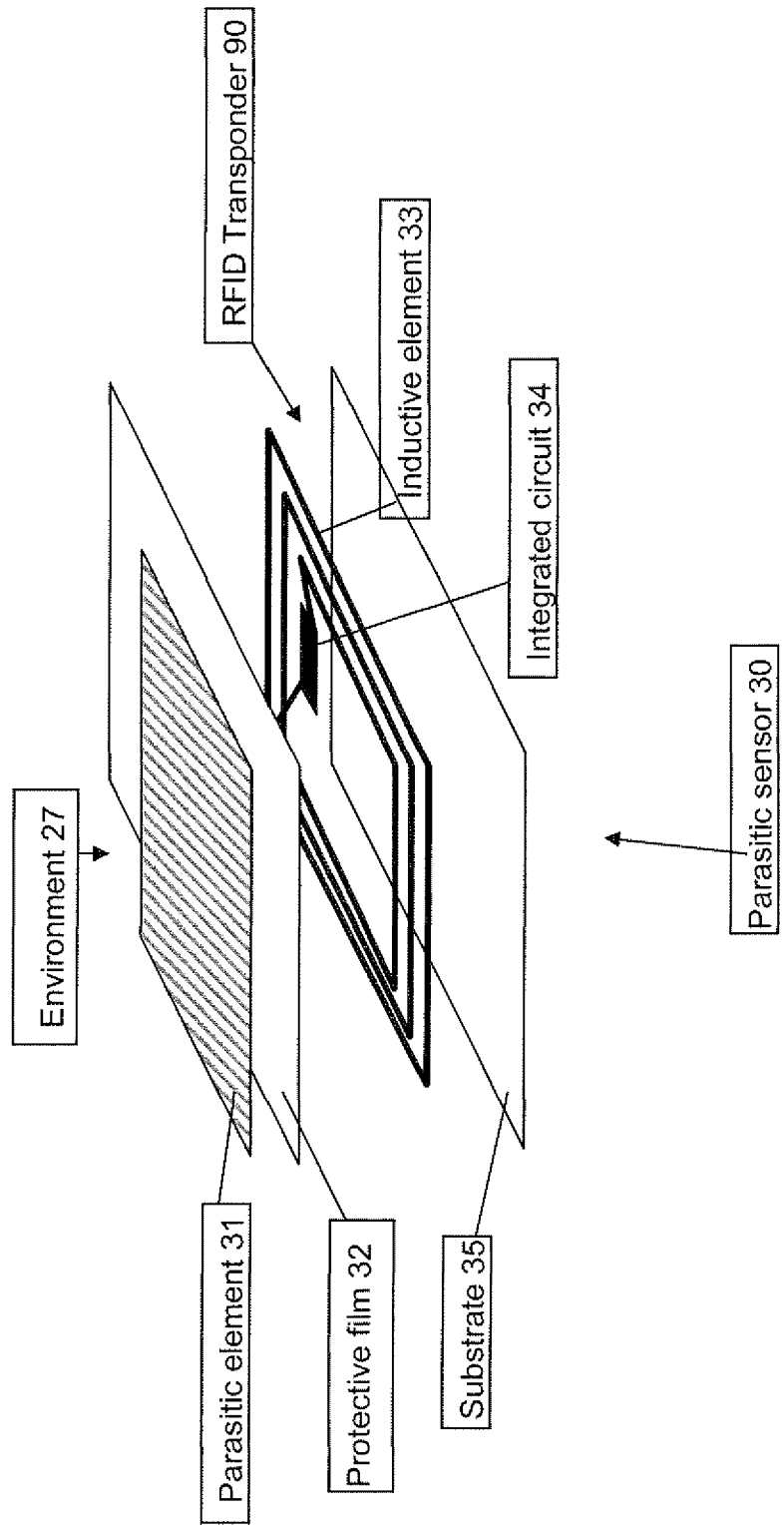
FIG. 2. Elements of the corrosivity sensor based on a parasitic sensor.
Figure 4:
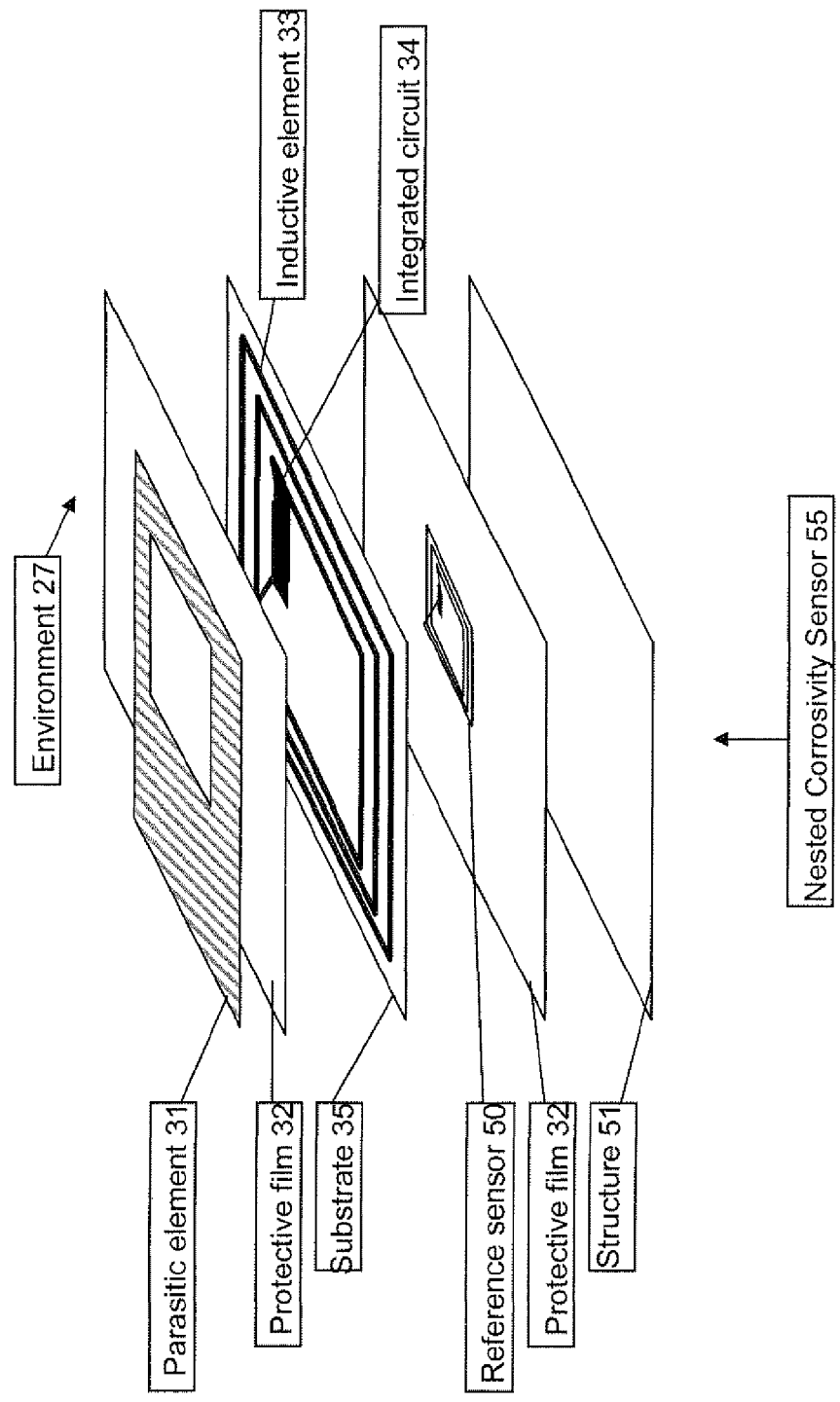
FIG. 4. Expanded view of corrosivity sensor layers for sensor tag and reference tag in a nested configuration.

Referring to FIGS. 2 and 4, the parasitic element (31) of the corrosivity sensor is exposed to the environment (27) that is being monitored. The parasitic element (31) is a metallic layer that is affixed to the protective film (32) in proximity to the inductive element (33) of the parasitic sensor (30), RFID transponder (90) and exposed directly to the environment (27). Exposure to the environment (27) alters the parasitic element (31) due to corrosion and degradation and thus changes the amount of power coupled to the reader from the RFID transponder (90) of the parasitic sensor (30).

Figure 5:
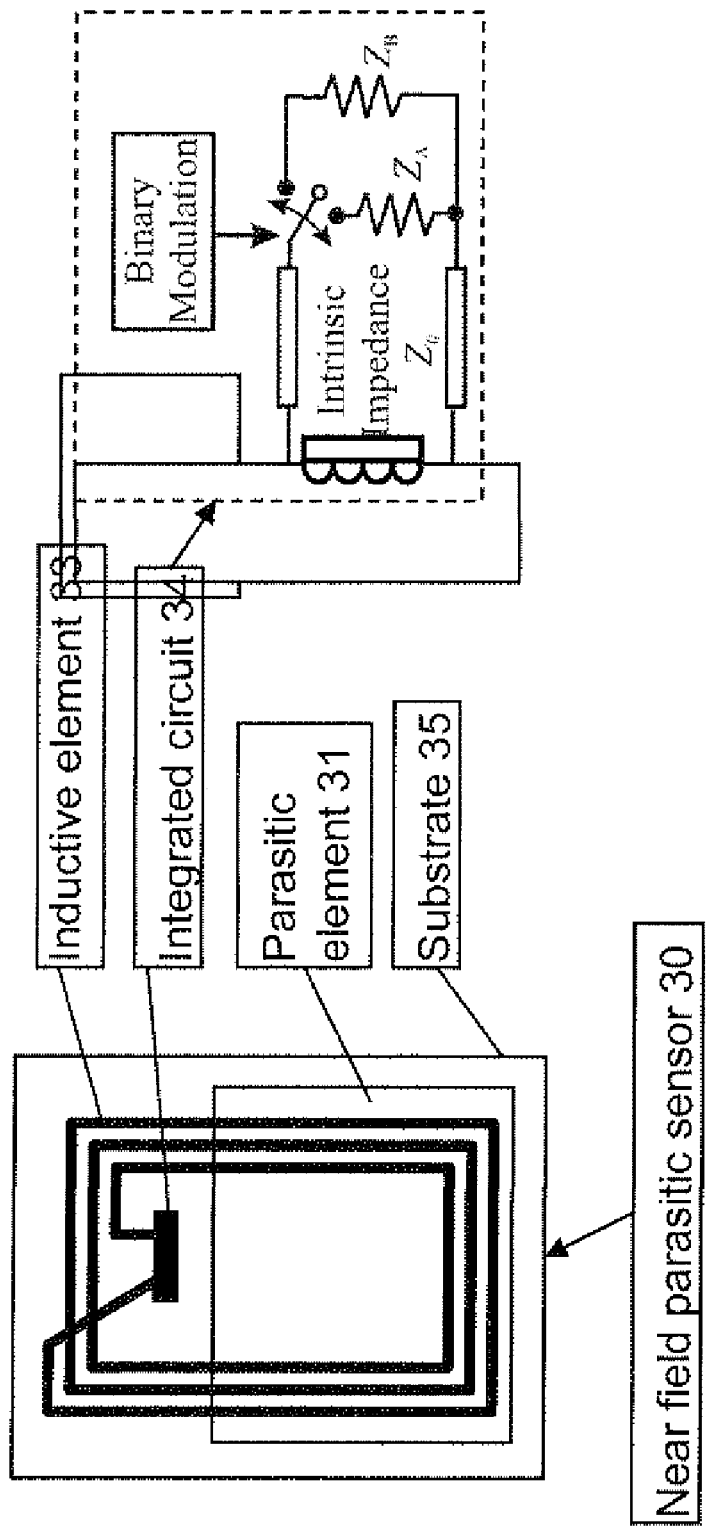
FIG. 5. Diagram of near field tag and microchip circuit diagram.

The parasitic element (31) in FIG. 2 may be any dielectric material, metal or alloy that can be formed into a thin film, tape or deposit on the substrate (35) or protective film (32) that is in proximity to inductive element (33) of the parasitic sensor (30). This may include, as non-limiting examples: metal and alloy films, foils or tapes of aluminum, copper or silver. Preferably, the parasitic element (31) is produced by vapor depositing metal or combinations of metals onto the protective film (32) to a predetermined thickness using vapor deposition techniques including but not limited to thermal, electron beam and chemical vapor deposition methods. The parasitic element (31) thickness can be 100 microns or less, 10 microns or less preferred, and 1 micron or less most preferred. In the most preferred embodiment, the thermal vapor deposited parasitic element (31) is a metal, copper or aluminum. The parasitic element (31) may be any geometry within, covering or outside the metal inductive element of the parasitic sensor (30). Preferably, for the nested corrosivity sensor (55) in FIG. 7, the arrangement of the parasitic sensor (30) and reference sensor (50), has the parasitic element (31) overlapping the inductive element (33) for the near field parasitic sensor of FIG. 5 and has an open area that does not cover the reference sensor (50), inductive element (33) or the area where the parasitic sensor (30) and reference sensor (50) inductive elements (33) overlap.

Figure 8:
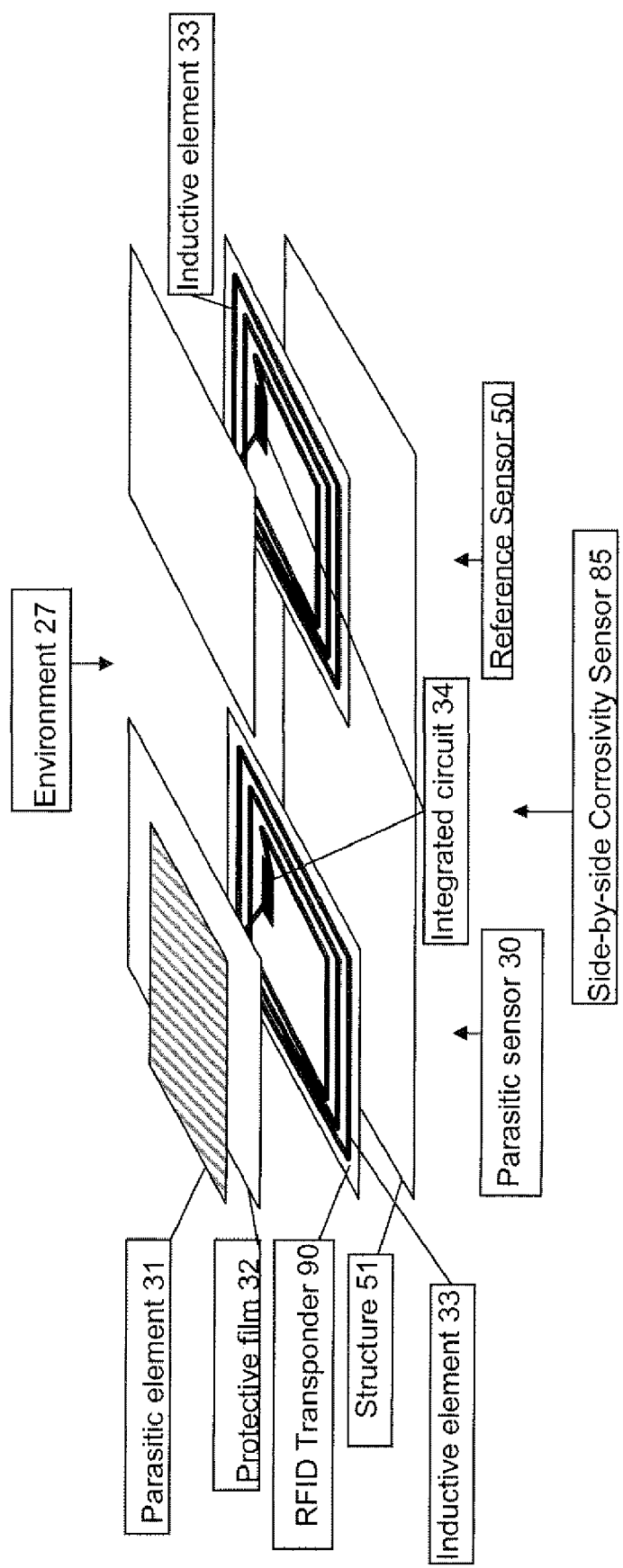
FIG. 8. Expanded view of corrosivity sensor layers for sensor tag and reference tag in a side-by-side configuration.

In a preferred example embodiment in FIG. 8, the parasitic element (31) is affixed to the protective film (32) that is a polymer film, coating or laminate such as but not limited to a polyester film, such as a polyethylene terephthalate (PET) film, polyamide or nylon film. This protective film (32) supports the parasitic element (31) and protects the inductive element (33) and integrated circuit (34) from environmental degradation. In this way, corrosion of the parasitic element (31) may proceed without other environmental factors such as corrosion of the other parasitic sensor (30) components and reference sensor (50) affecting the corrosivity sensor (26) response. The protective film (32) with parasitic element (31) is adhered to the RFID transponder (90) of the parasitic sensor (30).

In FIG. 8 the side by side corrosivity sensor (85), including parasitic element (31), protective film (32), and RFID transponders (90) for the parasitic and reference sensors (30 and 50), can be directly applied to a surface of the structure (51) or vehicle in a non-limiting side-by-side configuration. Preferably, the parasitic and reference sensors (30 and 50) are bonded to additional protective film (32) for enhanced durability and environmental resistance and then bonded to the structure or vehicle of interest.

Figure 7:
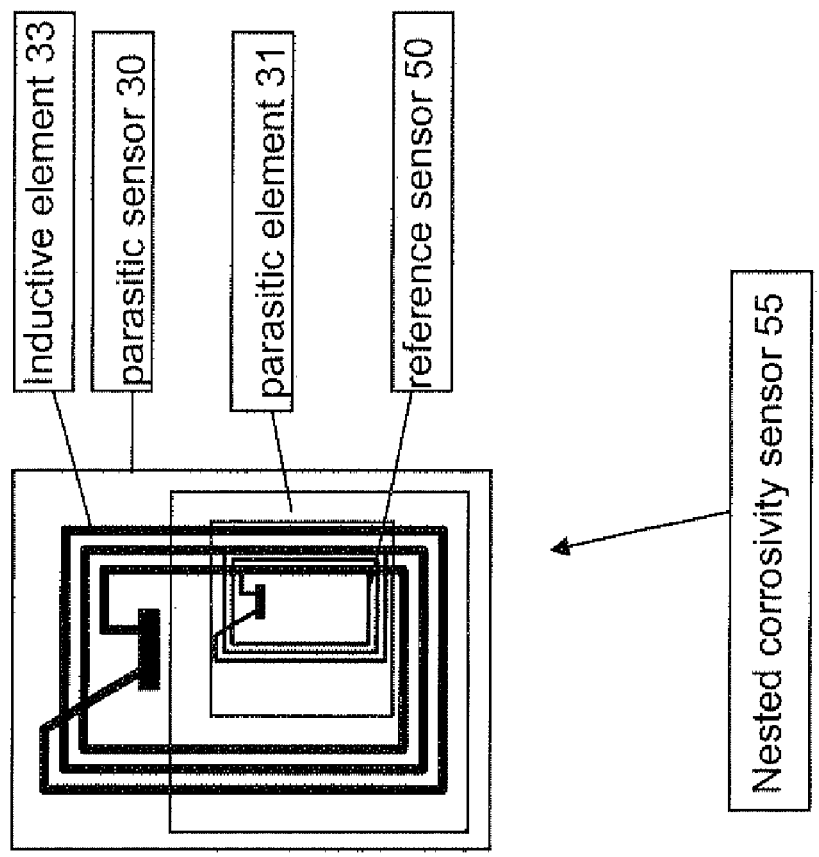
FIG. 7. Nested near field sensor tag and reference tag configuration for corrosivity sensor.
Figure 9:
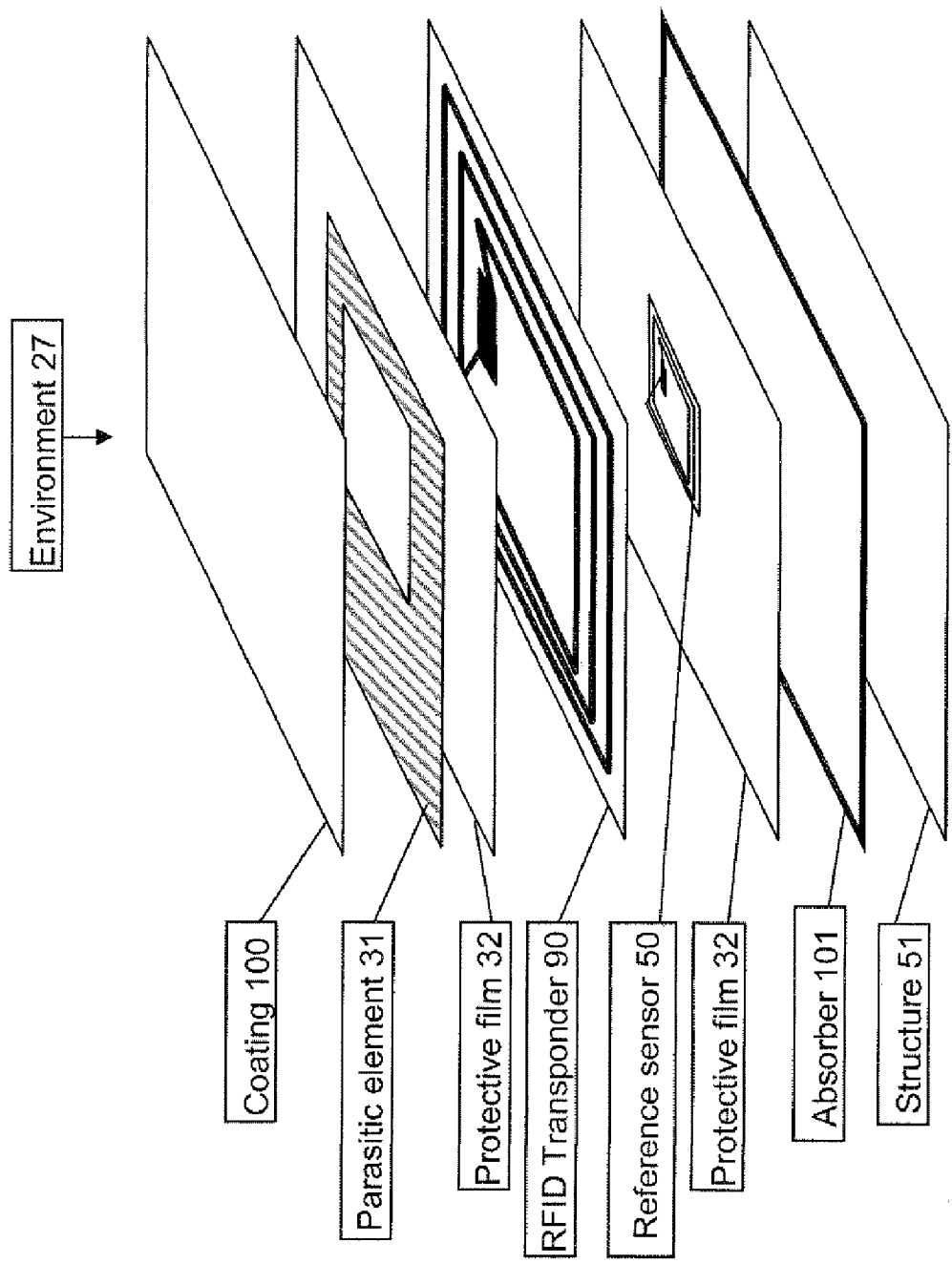
FIG. 9. Expanded view of corrosivity sensor layers for sensor tag and reference tag in a nested configuration with a coating applied over the parasitic element and absorber layer for use on metal substrates.

For the example embodiment of the nested corrosivity sensor configuration (55) for the parasitic and reference sensors (30 and 50) in FIG. 7, the corrosivity sensor layers include the parasitic element (31), protective film (32), RFID transponder (90), reference sensor (50), and protective film (32) as shown in FIG. 9. It is understood that the RFID transponder (90) and reference sensor (50) order may be reversed or otherwise varied. For use of the corrosivity sensor (26) on metal surfaces of structures and vehicles, a separating layer of dielectric material, absorbing material, absorber (101) or magnetic material is added between the RFID transponders and the surface of the structure (51) or vehicle, an example of which is shown in FIG. 9. Preferably, the absorber (101) is placed between the RFID transponder and the protective layer (32). An example absorber material is an ECCO-PAD® type product from Emerson & Coming Microwave Products.

Preferably, a reference sensor (50) is used as part of the corrosivity sensor (26) to accurately eliminate the uncontrolled variables that can be associated with measuring the corrosivity sensor (26) response such as distance and orientation between sensor and reader antenna, polarization, scattering and radiation of nearby objects, environmental factors such as humidity and temperature, and variations in the surface of the substrate. A variety of arrangements for the corrosivity sensor (26) are possible including a side-by-side arrangement (85) in FIG. 8 of the reference and parasitic sensors (50 and 30), or preferably a nested arrangement (55) for the near field corrosivity sensor in FIGS. 4 and 7. The nested arrangement decreases the total planar area of the corrosivity sensor (26) and improves the consistency of the near field measurement, since the coupling occurs only when the reader antenna (21) is located over the overlapped sections of the reference sensor and parasitic sensor inductive elements that are not covered by the parasitic element.

Optionally as in FIG. 9, the corrosivity sensor (26) may be covered with a coating (100) or coating system, such as a primer and topcoat, when the condition of the coating (100) subjected to environmental conditions is to be monitored. The coating (100) forms a barrier between the parasitic element (31) and the environment (27). Otherwise, the parasitic element (31) is directly exposed to the environment (27) that is to be monitored for corrosivity. The coating can be applied to the corrosivity sensor (26) before or after installation on the structure (51) or vehicle to be monitored. The corrosivity sensor (26) including parasitic element (31) is coated with the coating protection system (100) of interest.

The corrosivity sensor (26) of FIG. 1 and layers that form the corrosivity sensor in FIG. 9, including the protective films (32), absorber (101) and RFID transponders are bonded together and fixed to the structure (51), component or vehicle of interest. Bonding can be accomplished using adhesives and combinations of adhesives, including pressure sensitive adhesives, thermoplastic, or thermoset adhesives that include but are not limited to polyurethanes, acrylics, epoxies, cyanoacrylates, or silicones.

Measurement of corrosivity is accomplished by using a reader (22) to interrogate the corrosivity sensor (26) that incorporates the RFID transponder (90) and, when present, reference sensor (50). As the material of the parasitic element (31) is removed or corroded, the response of the parasitic sensor (30) is altered. The reference sensor (50) is unaffected by changes in the parasitic element and can be used to null out all other uncontrolled environmental factors, other than those associated with changes to the parasitic element. In this way, the corrosivity sensor (26) can be used to determine total cumulative damage or corrosive attack to the parasitic element (31) at any point in time when interrogated with the reader.

Figure 3:
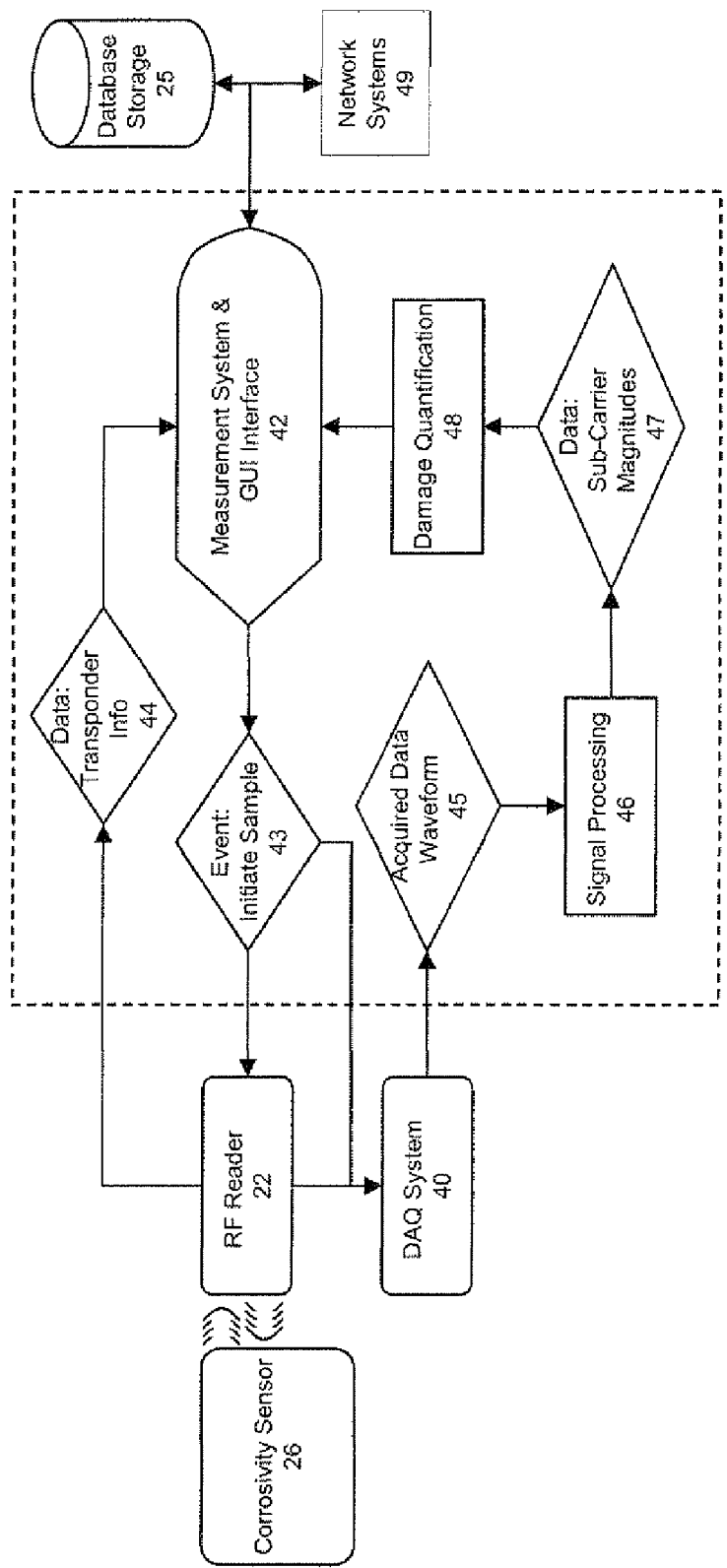
FIG. 3. Process elements of the corrosivity measurement system.
Figure 10:
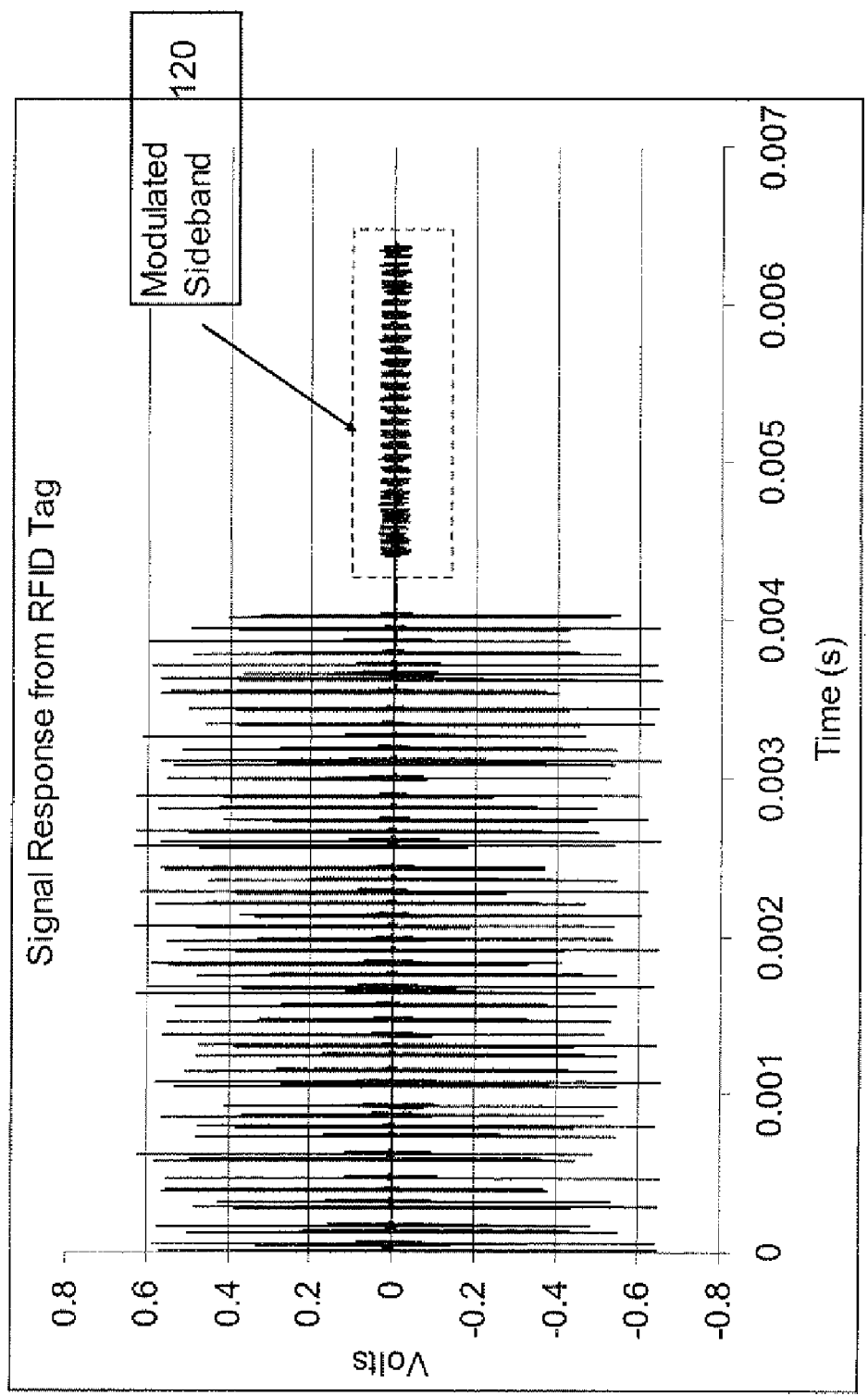
FIG. 10. Signal response from an RFID tag.
Figure 11:
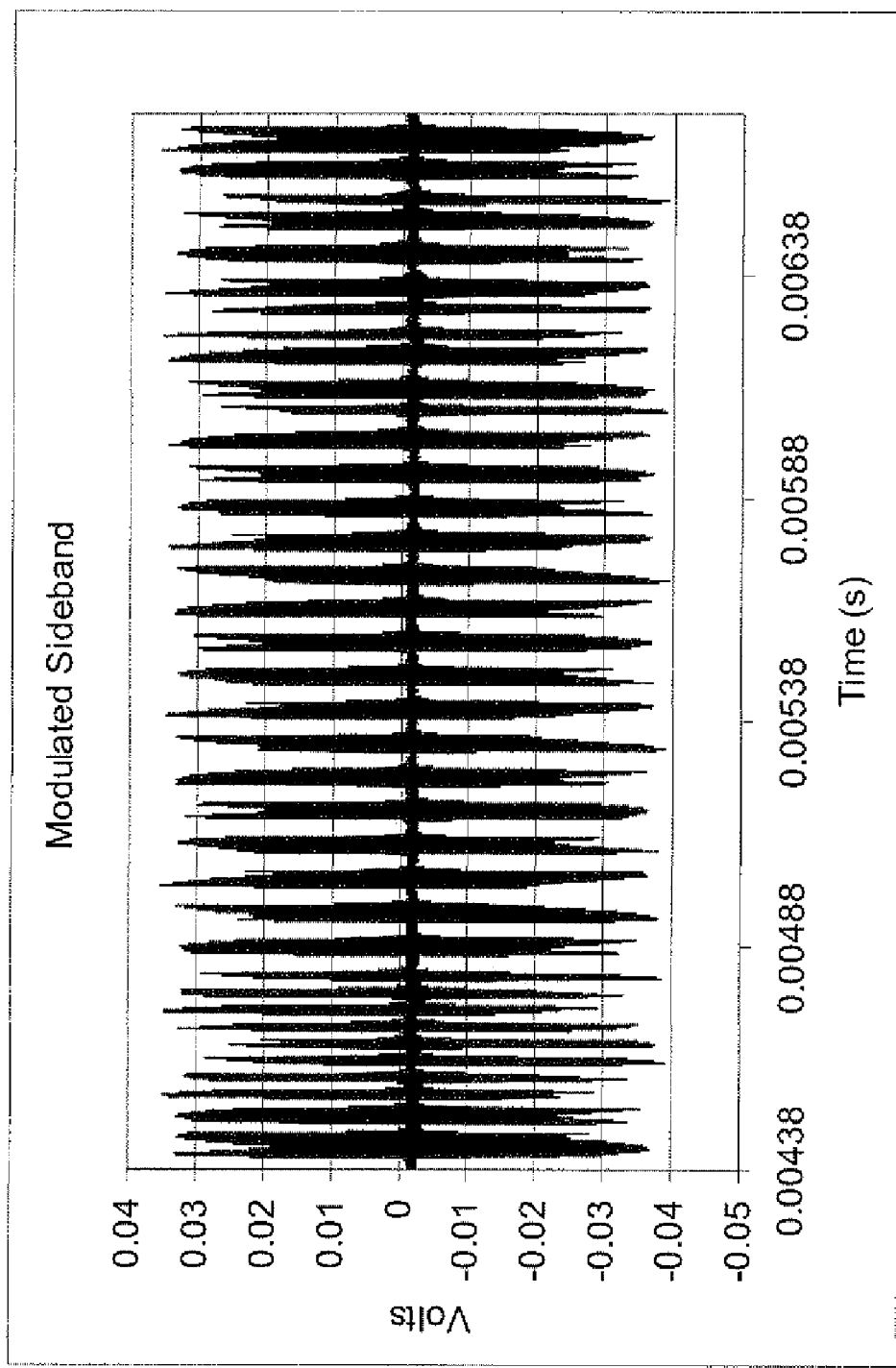
FIG. 11. Modulated side band signal response from and RFID tag.
Figure 12:
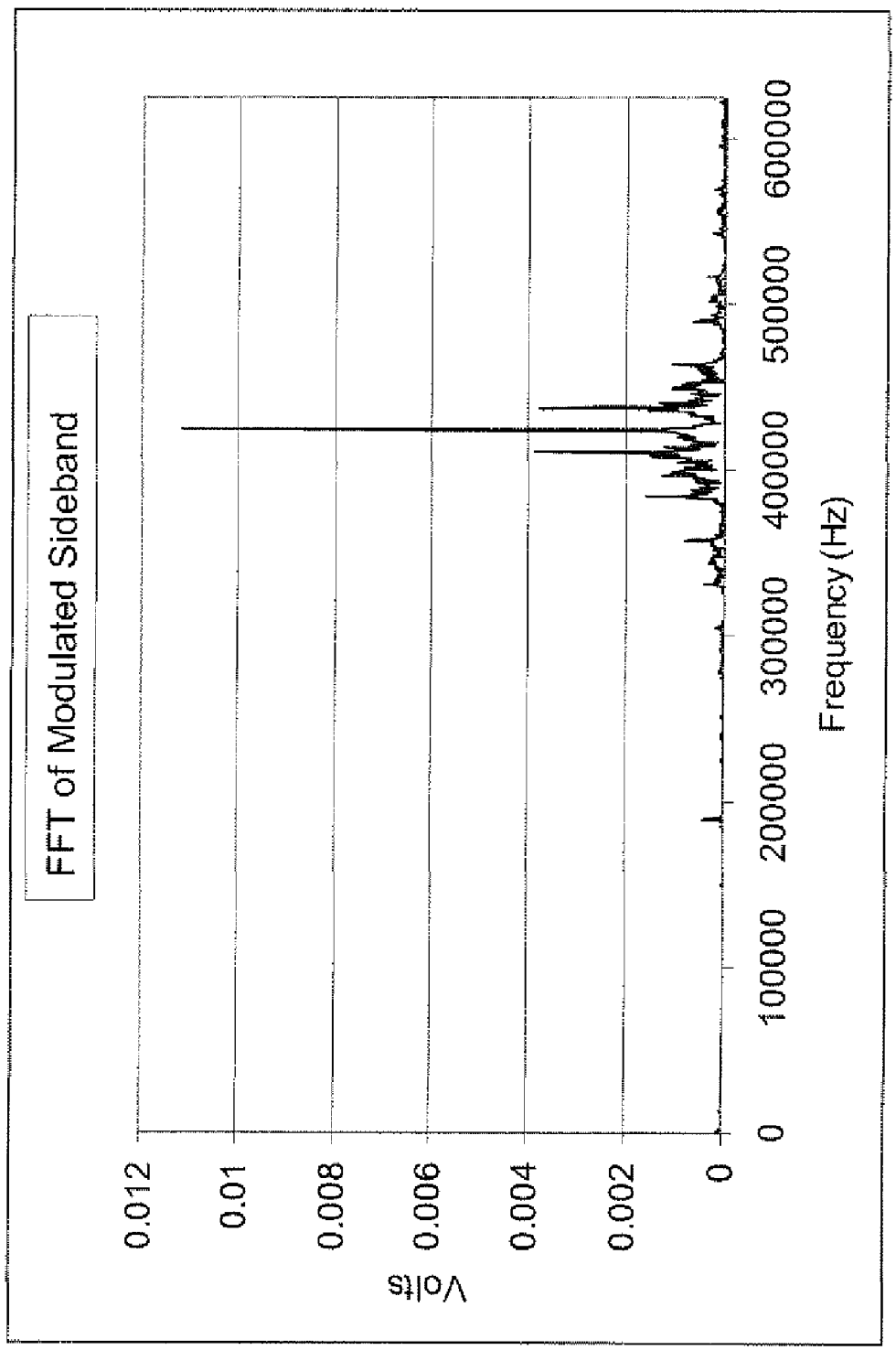
FIG. 12. Fast Fourier transform of modulated side band signal response from and RFID tag.

Referring now to FIG. 3, the corrosivity measurement is initiated (43) through a user interface (42) such as a graphical user interface that triggers the reader (22) and activates the data acquisition system (40). The corrosivity sensor (26)

response includes acquired waveforms from the reference sensor (50) and parasitic sensor (30) that contain unique transponder identification information (44) and the waveform signals (45) that can be used to quantify degree of corrosion of the parasitic element (31) shown in FIG. 11. The reader (22) can differentiate between and control the integrated circuits (34) of the parasitic sensor (30) and reference sensors (50) using the identification information (44) stored on the integrated circuits (34). Signal processing (46) is performed to determine the magnitudes of the parasitic sensor (30) and reference sensor (50) signals to quantify the corrosion or damage state (48) of parasitic element (31). Preferably signal processing (46) includes separating the sub-carrier modulated waveforms (47) and calculating their magnitude for determining damage state (48) of the parasitic element (31). A damage state (48) may be determined by comparing the magnitude of the parasitic sensor (30) response to the known full scale response of the parasitic sensor (30) without the parasitic element (30). Preferably the damage state (48) of the parasitic element (31) is determined from the magnitude of the parasitic sensor (30) response normalized to the reference sensor (50) response. The RFID transponders (90) of the parasitic sensor (30) and reference sensor (50) powered by the electromagnetic field of the reader (22) produce a modulated waveform response that is detected by the reader (22) shown in FIG. 11. As the parasitic element (31) degrades or corrodes due to the environment (27), the magnitude of the parasitic sensor (30) response increases relative to the reference sensor (50). In FIG. 10 the magnitude of the modulated side band (120) responses of the parasitic sensor (30) and reference sensor (50) are used to quantify the corrosion damage. A non-limiting example of the magnitude calculation is to perform a fast Fourier transform (FFT) on the modulated side band (120) and utilize the peak value of the center frequency as a magnitude measurement of the RFID transponder response as shown in FIG. 12.

A ratio of the parasitic sensor (30) to the reference sensor (50) magnitudes provides a unitless, normalized measure of the corrosivity. When the parasitic element (31) is completely corroded, the intensity of the parasitic sensor (30) response peaks and is fixed relative to the reference sensor (50).

Figure 14:
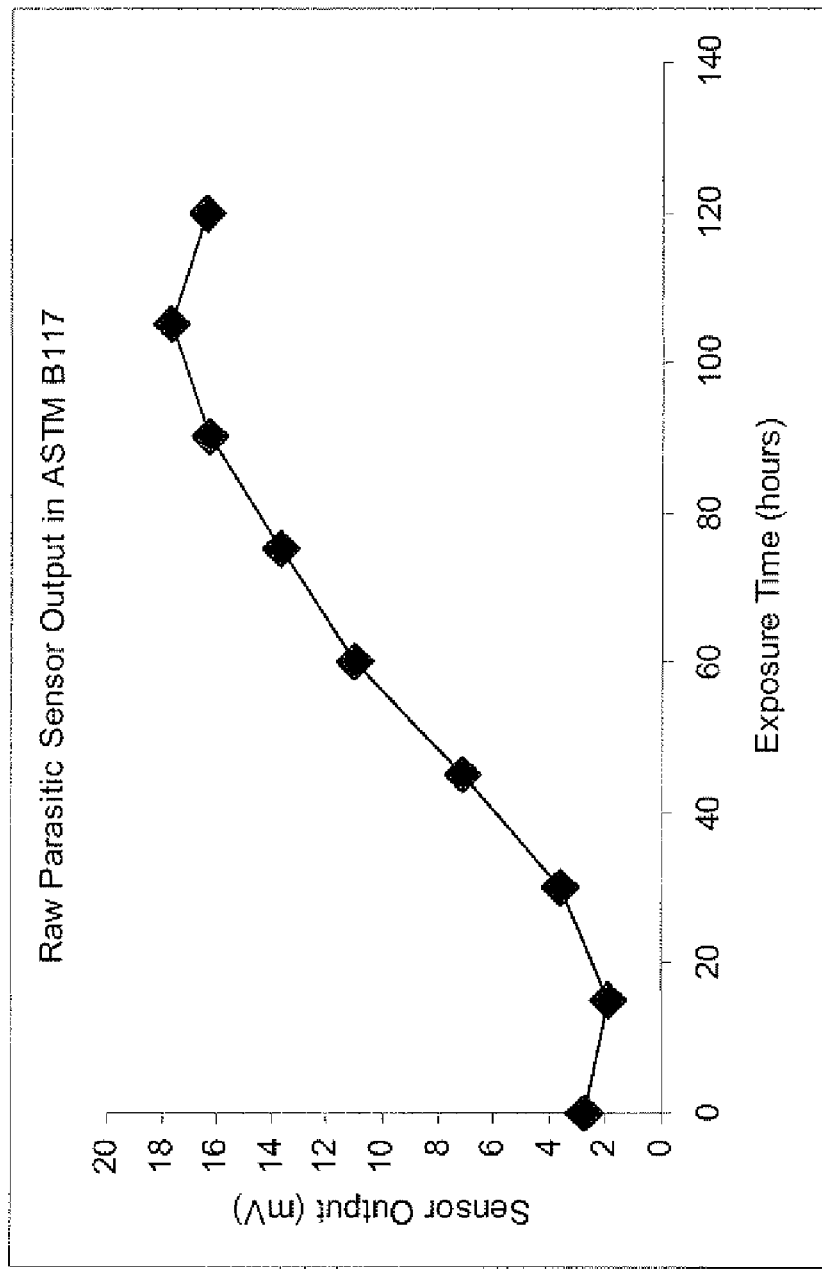
FIG. 14. Parasitic sensor response as a function of time of exposure in ASTM B117 salt spray test.
Figure 15:
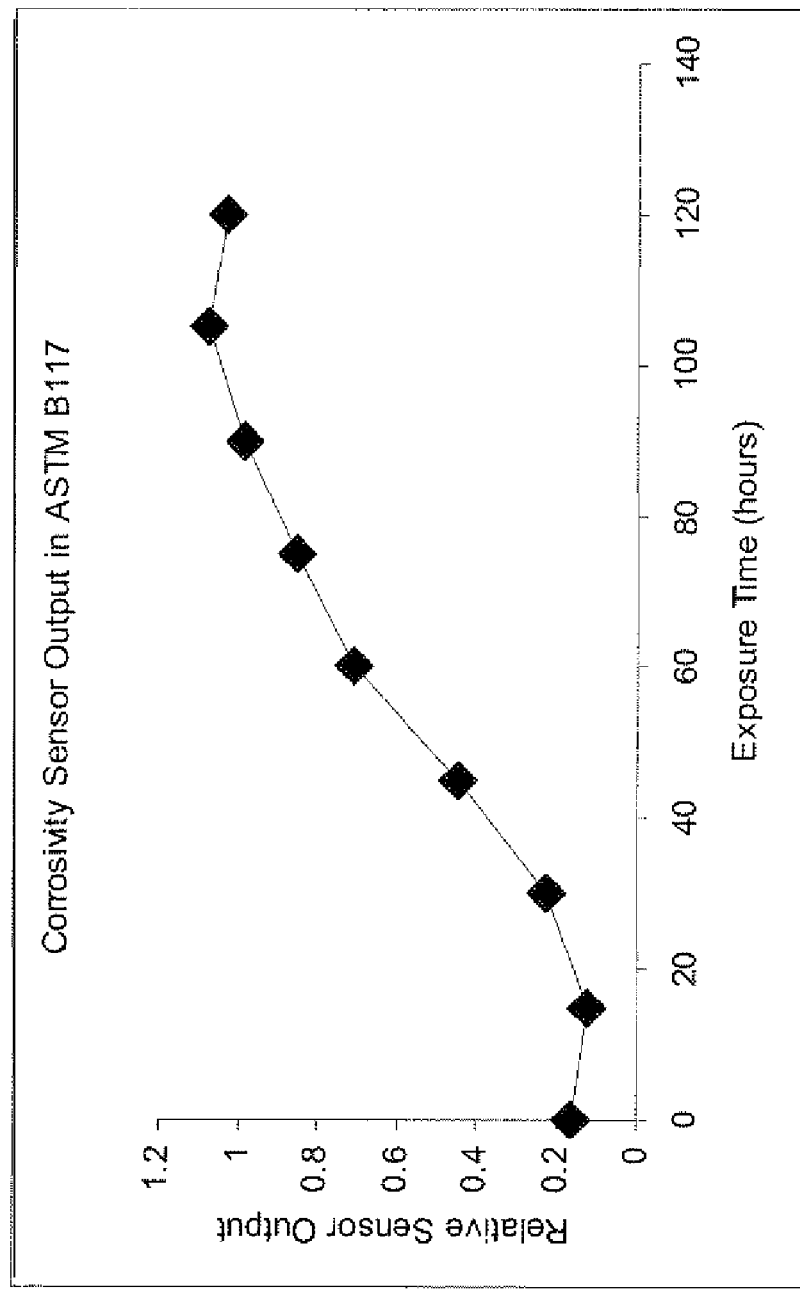
FIG. 15. Corrosivity sensor response (ratio of parasitic sensor to reference sensor) as a function of time of exposure in ASTM B117 salt spray test.

The corrosivity data and specific sensor transponder identification information is stored in a data storage (25) that is available to local and network users. The data as shown in FIGS. 14 and 15 may be displayed as a time based trend chart, or provide an audible or visual alarm as to the need for inspection and maintenance of the structure or vehicle. The data storage (25) information is useful for tracking cumulative corrosivity and environmental severity that a structure (51), component or vehicle has experienced.

The corrosivity sensor (26) is based on radio frequency identification (RFID) transponders (90) that contain microchip integrated circuits (34) and inductive element (33) metal inlays mounted on a substrate (35). These RFID transponders (90) transmit data to the reader system (22) for corrosivity measurement and unique identification for sensor tracking. The RFID transponders are commercially available, such as those RFID transponders from Texas Instruments for operation at 13.56 MHz and 860-960 MHz. A preferred example embodiment uses the Tag-it™ HF-I Standard Transponder and Chip/Inlays such as RI-102 and RI-103 type RFID transponders.

Readers (22) are used to interrogate the sensors and make the sensor information available to the data processing unit for correlation to environmental effects. In the case when an integrated circuit (34) is present, the reader will have the information from the integrated circuit (34) available in digital format. The reader (22) may also be used to program, enable or disable, and supply power to the sensors and sensor integrated circuits. Readers may include hardware, software, and antenna(s) (21) that are required to communicate with the sensor and obtain the sensor information. The reader may contain one antenna (21) that acts as both a transmitter and receiver or it may have two separate antennas that perform the two functions. The transmissions can be done simultaneously or sequentially. Readers (22) are available for interrogating RFID transponders, an example of such can be obtained from Texas Instruments or FEIG Electronic GmbH. Compatible reader antennas (21) can be obtained from MetraTec RFID solutions.

Such readers allow for easy tracking of a large inventory of sensors (26) for management of structures (51), components, facilities and vehicles for corrosion and condition monitoring. In addition, the integrated circuits (34) of the RFID transponders (90) are capable of storing information that may be of interest such as previous measured data, date of last measurement, vehicle, component or structure (51) identification, and coating (100) identification. A preferred example embodiment does not require a determination of the resonant frequency of the parasitic element but depends simply on the amplitude or intensity of the electromagnetic response of the RFID transponder. The corrosivity sensor (26) uses the available electromagnetic waveform response of the passive RFID transponder (90) to the reader excitation. The waveform of the reader (22) is obtained by accessing the analog signal at the demodulated integrated circuit of the reader (22). The waveform is collected and stored with an external data acquisition system (40). Rather than specifically monitoring resonant frequency shifts or changes in Q values of the parasitic element, only the intensity or amplitude of the coupling or backscatter from the sensor (26) is needed to measure corrosivity.

The technology may utilize either near field or far field RFID transponders to form the parasitic and reference sensors. The far field example embodiment (74) in FIG. 6 allows the corrosivity sensor to be interrogated at a distance of several meters, which may be important in some applications. Far field refers to the condition where the received wave fronts between the reader and RFID transponders are essentially planar. In this example embodiment, the reader (22) communicates with the sensor (74) by far field electromagnetic radiation and backscatter. The reader (22) illuminates the sensor (74) with an electromagnetic field, and the sensor (74) communicates with the reader (22) through electromagnetic backscatter. As the parasitic element (31) changes, the backscatter efficiency is altered, and this change is used as a measure of damage accumulation. In a preferred example embodiment, a near field system measures the efficiency of the inductive coupling between the reader antenna (21) and the inductive element (33) of the RFID transponder (90) of the parasitic sensor (30) and the reference sensor (50). Near field indicates that the electromagnetic waves received by the corrosivity sensor (26) are not planar, i.e., they have significant curvature. The parasitic element (31) interferes with the coupling between the reader antenna (21) and inductive element (33) of the RFID transponder (90) of the parasitic sensor (30). As the parasitic element (31) corrodes or is otherwise removed, the intensity of the parasitic sensor's (30) response increases due to improved coupling between the parasitic sensor (30) and the reader (22).

The near field sensors contain resonant circuit elements in the integrated circuit (34) that are activated by electromagnetic energy and use the energy to transmit information. Each sensor contains an integrated circuit (34) that can store digital information that may be written to and/or read by the reader. Example integrated circuits (34) are Texas Instruments GEN 2 UHF and Tag-it™ HF-I Plus Transponder chip product families. The data is modulated onto the signal returned by the sensor.shown in FIG. 11.

Figure 6:
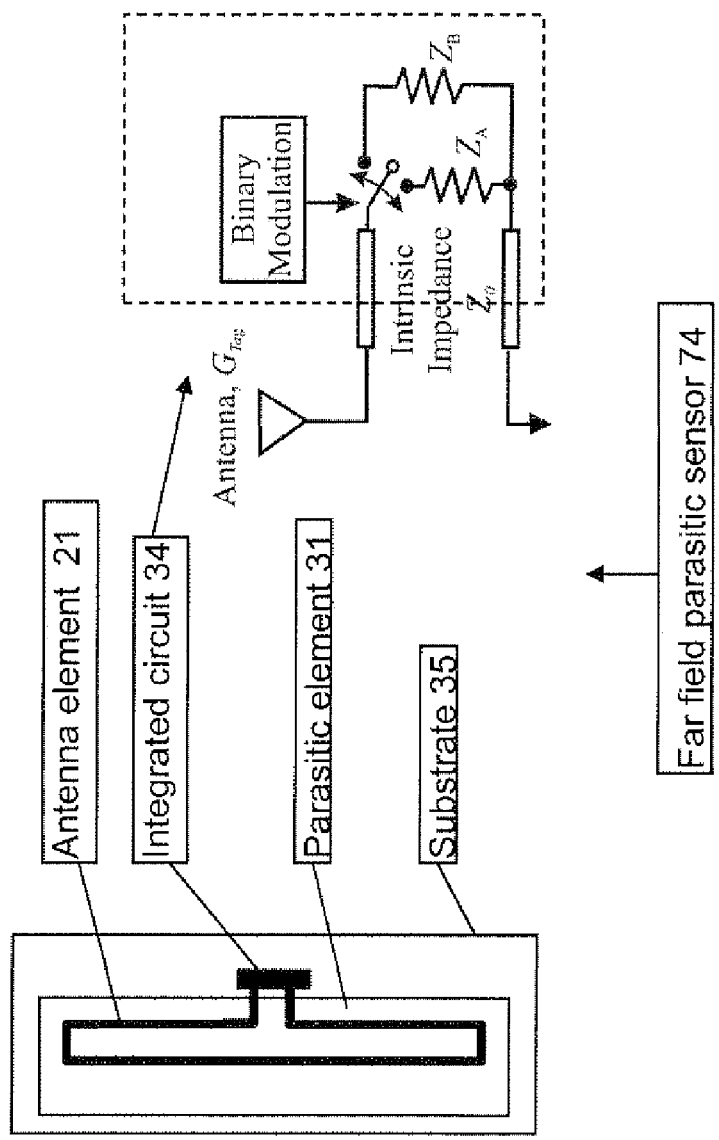
FIG. 6. Diagram of far field tag and microchip circuit diagram.

The far field sensors contain antenna elements (21) in FIG. 6 that are excited by an incident electromagnetic wave and scatter this energy back to the reader. The far field sensors contain integrated circuits (34) that are powered by the energy captured by the antenna. The circuits may store digital information that may be written to and/or read by the reader (22). The data is modulated onto the electromagnetic wave that is scattered back to the reader (22). A parasitic or multiple parasitic elements (31) are used to sense environment factors. The parasitic element (31) is a conductor or dielectric that can be placed near antenna, above, or covering the antenna element (21). As the parasitic element (31) is exposed to the environment (27), the properties of the parasitic element (31) change which alters the amount of power scattered by the antenna element (21). A preferred example embodiment for the corrosivity sensor is to have two RFID transponder elements, one of which functions as a parasitic sensor (30) and the other the reference sensor (50). The parasitic sensor (30) and reference sensor (50) are protected from the environment using a protective film (32), with only the parasitic elements (31) exposed. The reader (22) differentiates between the parasitic sensor (30) and reference sensor (50) by differences in the identification information modulated on the backscattered signal by the integrated circuit (34). The sensor may possess its own ground plane or use the surface of the structure (51) as the ground.

Several non-limiting examples are now described, for illustration purposes only, relating to free space measurements, measurements made on metal structure (51) using an absorber (101), and corrosivity sensors (26) tested without and with a coating. In each example, the corrosivity sensor consisted of a parasitic sensor (30) and reference sensor (50).

EXAMPLE 1

Figure 13:
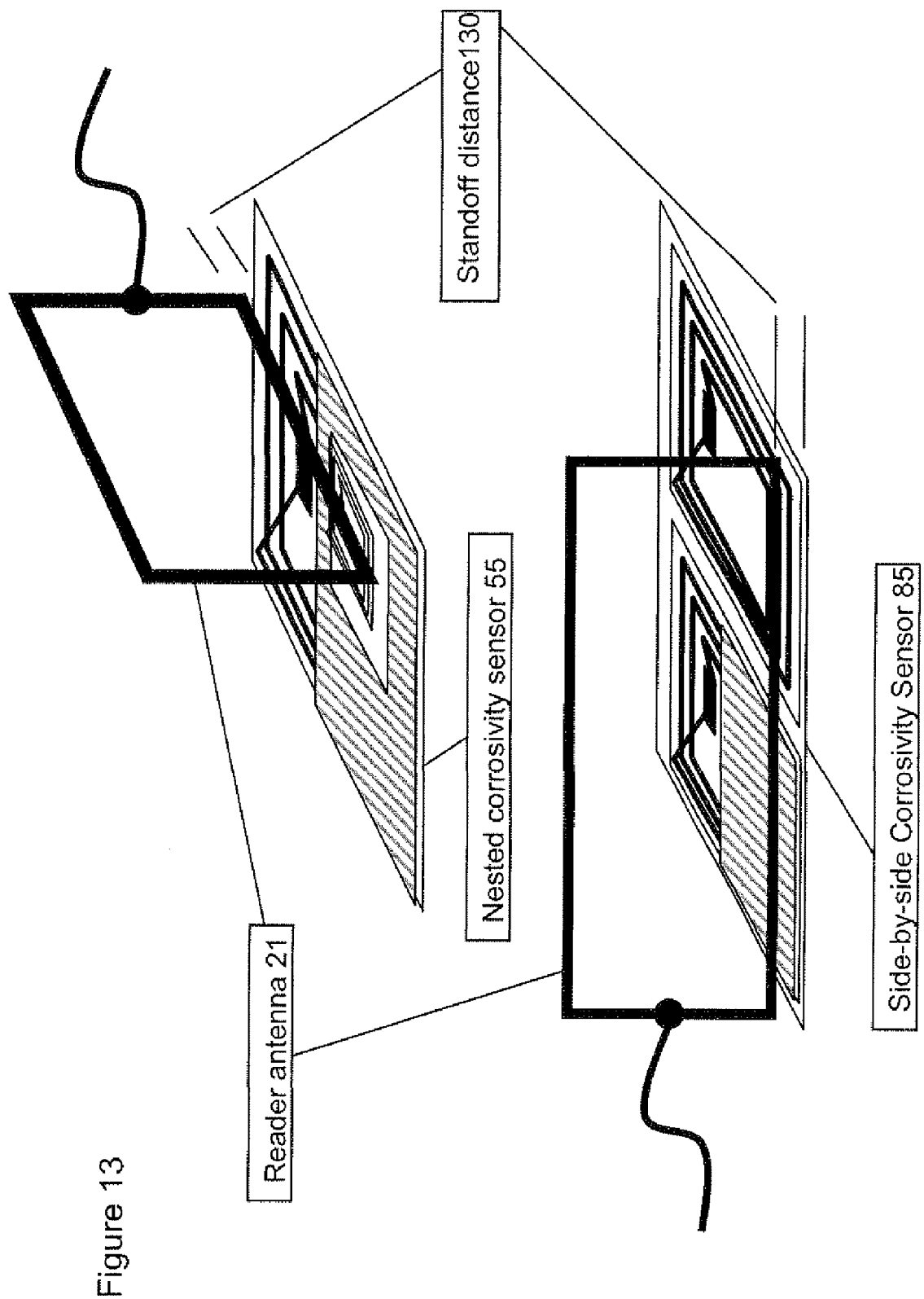
FIG. 13. Orientation of reader antenna to corrosivity sensor for near field readings.
Figure 16:
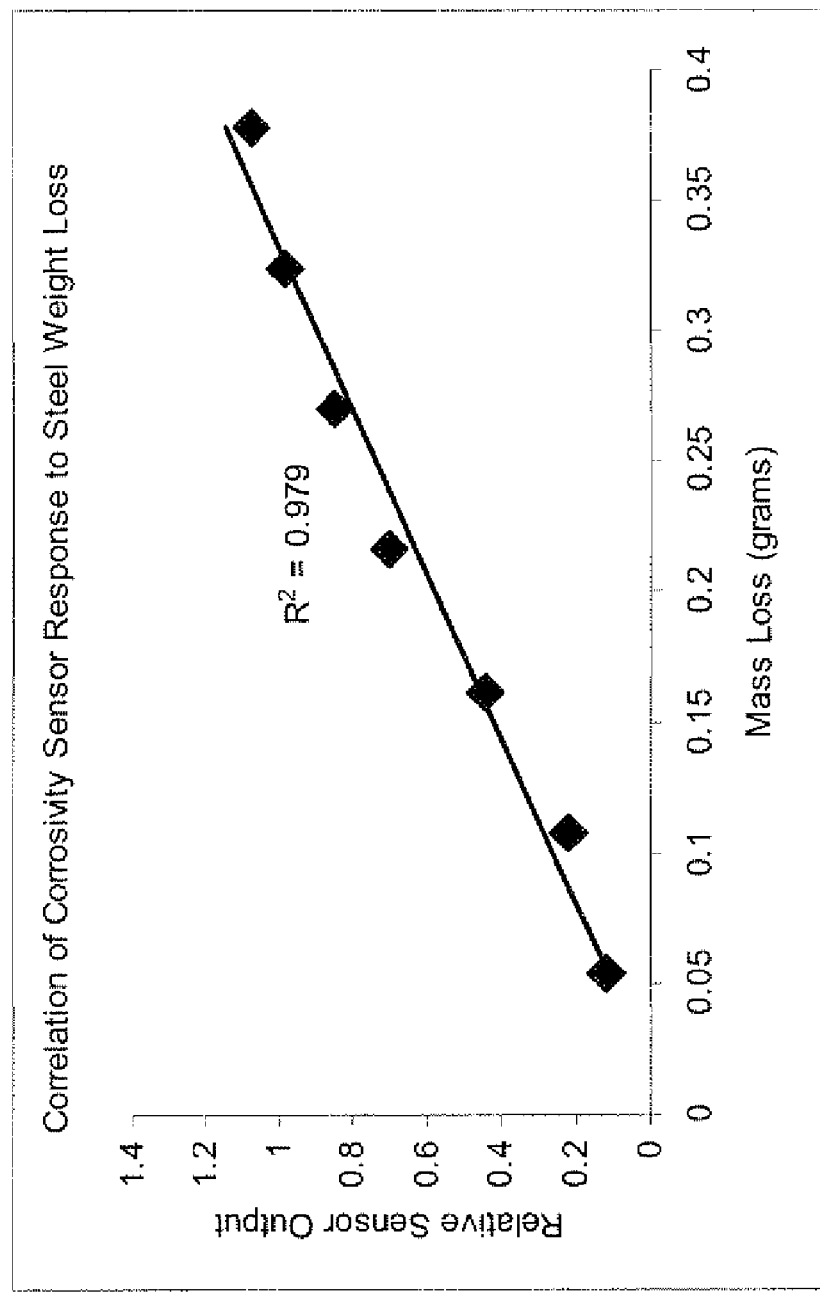
FIG. 16. Correlation of corrosivity sensor response (ratio of parasitic sensor to reference sensor) to steel weight loss coupons tested over the same time frame in ASTM B117 salt spray test.

ASTM B117 salt spray test were performed on a side-by-side corrosivity sensor (85) and 1010 low ally carbon steel weight loss coupons. The corrosivity sensor (85) had a side-by-side geometry similar to that shown in FIG. 8 and contained a parasitic sensor (30) and reference sensor (50). The RFID transponders used in the parasitic sensor (30) and reference sensor (50) were Texas Instruments, Tag-It™ HF transponders (13.56 MHz), model #: RI-I02-114A-01. The parasitic sensor (30) and reference sensor (50) were laminated between two protective polymer films (32) using a thermal laminator. The side-by-side corrosivity sensor (85) was masked, except for a rectangular area that encompassed two thirds of the inductive element (33) away from the integrated circuit (34) of the RFID transponder (90) for the parasitic sensor (30) as shown in FIG. 2. Copper was thermally deposited on the masked corrosivity sensor (85) to a thickness of approximately one micron. The mask was removed and the corrosivity sensor (26) was evaluated with the wireless measurement system (20) in FIG. 1. A Model #: ID ISC.MR101-A, Mfg: FEIG Electronic GmbH reader (22) was used with a Model #: MaxiPCB, MetraTec RFID Solutions antenna (21) to read the corrosivity sensor (85) composed of the side-by-side parasitic sensor (30) and reference sensor (50). As shown in FIG. 13 the standoff distance (130) between the reader antenna (21) and the corrosivity sensor (85) was approximately 0.25 inches with an orthogonal orientation similar to that shown in FIG. 13 between the reader antenna (21) and corrosivity sensor (85). The reader interrogation measurements were performed with the corrosivity sensor (85) mounted on an eighth inch thick piece of polyethylene sheet. After measuring the corrosivity sensor (85) response with the reader (22), the corrosivity sensor (85) was placed into the ASTM B117 test cabinet with the steel weight loss coupons. Periodically, the corrosivity sensor (85) was removed and interrogated with the reader (22) as described above and then returned to the salt spray cabinet. Also periodically, steel weight loss coupons were removed over the same test timeframe. The steel weight loss was measured according to ASTM-G1 Practice for Preparing, Cleaning, and Evaluating Corrosion Test Specimens. The magnitude of the parasitic sensor (30) response and the ratio of parasitic sensor (30) response to reference sensor (50) response are dependent on the time of exposure in ASTM B117 salt spray as shown in FIGS. 14 and 15. Furthermore, the corrosivity sensor (85) response determined from the ratio of the parasitic sensor (30) response to reference sensor (50) response strongly correlates to the steel weight loss in FIG. 16. The example demonstrates the use of the corrosivity sensor (85) to monitor a corrosive environment and predict corrosion damage to a metal or alloy structure (51) in the same environment.

EXAMPLE 2

Figure 17:
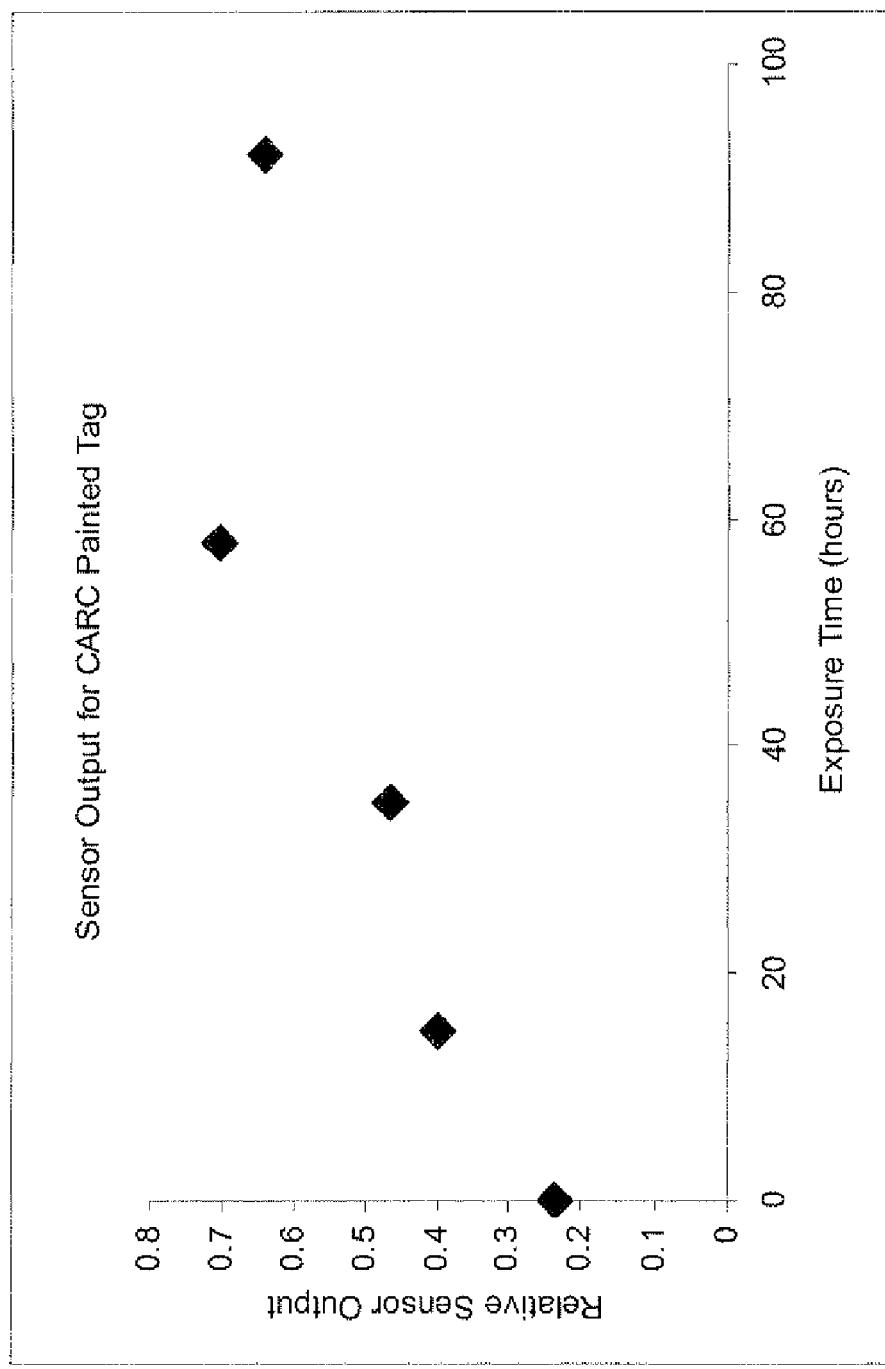
FIG. 17. Time based response of corrosivity sensor response (ratio of parasitic sensor to reference sensor) mounted on an aluminum alloy sheet and coated with a military chemical agent resistant coating (CARC) coating system. Mounted and painted sensor was exposed to accelerated UV and ASTM B117 salt spray corrosive testing.

Corrosivity sensor (55) with a paint coating (100) was tested in a combination of modified ASTM G154-06 UV exposure test and ASTM B117 salt spray. The test was performed on a corrosivity sensor (55) that had a nested parasitic sensor (30) and reference sensor (50) geometry similar to that shown in FIG. 9. The RFID transponders (90) used in the corrosivity sensor included a parasitic sensor (30) with a Texas Instruments, Tag-It™ HF transponder (13.56 MHz), model #: RI-I02-114A-01 and reference sensor (50) with a Texas Instruments, Tag-It HF (13.56 MHz), model #: RI-I03-114A-01. The reference sensor (50) RFID transponder (90), parasitic sensor (30) RFID transponder (90), and absorber material (101) were laminated between two protective polymer films (32) using a thermal laminator. The absorber material (101) was ECCOPAD HFH-30/DSS-6M, Mfg: Emerson & Corning Microwave Products, thickness: 0.030 inches. The absorber (101) separated the corrosivity sensor (55) RFID transponders (90) from the structure material (51) AA2024-T3 aluminum alloy sheet. After laminating, the corrosivity sensor (55) was masked to achieve a patterned metallic vapor deposit similar to that shown in FIG. 9 for the parasitic element (31). Once the corrosivity sensor (55) was masked, aluminum was thermally deposited on the masked corrosivity sensor (55) to a thickness of approximately one micron. The mask was removed and the corrosivity sensor (55) was adhered to a four inch by six inch by 0.03 inch thick aluminum sheet using a high strength pressure sensitive adhesive VHB™ Tape, Product #: VHB-4905, 3M™. The corrosivity sensor (55) mount on the aluminum sheet coated with a two coat paint system (100) consisting of a two component off-white high solids epoxy primer, MIL-P-53022B, 04488WEP-4/04489CEH-4, and two component water reducible 383 green CARC topcoat, MIL-DTL-64159 Type I, 07770GWU/0775CMU both from Hentzen Coatings, Inc. After curing for more than seven days, the painted corrosivity sensor (55) mounted on aluminum structure (51) was exposed to 50 hours of an ASTM G154 test cycle (step 1—UV exposure at 0.48 $W/m^2$ at 60° C. for 4 hours, and step 2—water condensation with no UV irradiance at 40° C. for 4 hours) followed by 8 hours of ASTM B117 salt spray and then returned to ASTM G154 test for a total test duration of 92 hours. Periodically the paint aluminum panel with corrosivity sensor was interrogated with the wireless corrosions measurement system (20) described in Example 1 above. Standoff distance (130) between the reader antenna (21) and the corrosivity sensor (55) was approximately 0.25 inches with an orthogonal orientation between the reader antenna (21) and corrosivity sensor (55) similar as shown in FIG. 13. The magnitude of the parasitic sensor (30) response and the ratio of parasitic sensor (30) response to reference sensor (50) response are dependent on the time of exposure as displayed in FIG. 17. The example demonstrates the use of the corrosivity sensor (55) to monitor coating system breakdown in a high UV and corrosive environment on a metal structure (51).

As mentioned above, a preferred example embodiment is the near field system that measures the intensity of the inductive coupling between the reader antenna (21) and the inductive element (33) of the RFID transponder (90) of the parasitic sensor (30) and the reference sensor (50). A nested arrangement of the parasitic sensor (30) and reference sensor (50) is used for this example embodiment of the near field corrosivity sensor (26). The corrosivity sensor (26) includes a layer of absorbing material for use on metal surfaces of structures and vehicles. Corrosion state of the parasitic element (31) is determined from the magnitude of the parasitic sensor (30) response normalized to the reference sensor (50) response. Each of the parasitic (30) and reference sensors (50) contains an integrated circuit (34) and inductive element (33) that are activated by electromagnetic energy from the reader (22) used to transmit information between the reader (22) and corrosivity sensor (26). The integrated circuits (34) store digital information that can be written and/or read by the reader (22).

Although various example embodiments have been shown and described in detail, the claims are not limited to any particular embodiment or example. None of the above description should be read as implying that any particular element, step, range, or function is essential such that it must be included in the claims scope. Reference to an element in the singular is not intended to mean "one and only one" unless explicitly so stated, but rather "one or more." The scope of patented subject matter is defined only by the claims. The extent of legal protection is defined by the words recited in the allowed claims and their equivalents. All structural and functional equivalents to the elements of the above-described example embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. No claim is intended to invoke paragraph 6 of 35 USC §112 unless the words "means for" or "step for" are used. Furthermore, no feature, component, or step in the present disclosure is intended to be dedicated to the public regardless of whether the feature, component, or step is explicitly recited in the claims.

The invention claimed is:

1. A sensor for sensing an affect of an environment on a structure on or near which the sensor is located, comprising:
    a substrate;
    an inductive element formed on a substrate for receiving electromagnetic radiation with a particular electromagnetic response;
    a protective film that isolates the inductive element from the environment;
    a parasitic element proximate to the inductive element and having a first affect on the electromagnetic response,
    wherein as the environment interacts with and changes at least one characteristic of the parasitic element, the changed parasitic element has a second, different affect on the electromagnetic response that is detectable by a sensor reader to monitor changes to the structure.

2. The sensor in claim 1, wherein a difference between the first and second affects on the electromagnetic response corresponds to environmentally-induced changes to the structure.

3. The sensor in claim 1, wherein the change to the structure includes one or more of: corrosion, erosion, exposure, physical or chemical change, a cumulative damage, or degradation of the structure or a protective coating on the structure.

4. The sensor in claim 1, wherein the parasitic element may be any geometry within, covering, or outside the inductive element that is in close proximity to but electrically insulated from the inductive element.

5. The sensor in claim 1, further comprising:
    an integrated circuit connected to the inductive element enabling storage and communication of sensor information including one or more of: identification, date/time stamp, material description, or prior sensor measurements,
    wherein the integrated circuit is wirelessly powered by electromagnetic radiation received from the sensor reader via the inductive element.

6. The sensor in claim 1, further comprising:
    a material separating the sensor from the structure including an electromagnetic absorber or magnetic material in proximity to the sensor for operation on metallic structures.

7. The sensor in claim 1, further comprising:
    a coating on the parasitic element for monitoring a condition of a coating on the structure.

8. A sensing system comprising:
    a sensor for sensing an affect of an environment on a structure on or near which the sensor is located, the sensor including:
    a substrate,
    an inductive element formed on a substrate for receiving electromagnetic radiation;
    a protective film that isolates the inductive element from the environment;
    a parasitic element proximate to the inductive element; and
    an integrated circuit connected to the inductive element for enabling storage and communication of sensor information including one or more of: identification, date/time stamp, material description, or prior sensor measurements, wherein the integrated circuit is wirelessly powered by electromagnetic radiation received from the sensor reader via the inductive element, and
    a sensor reader including:
    one or more antennas,
    a transmitter, connected to the one or more antennas, for transmitting electromagnetic radiation that interacts with the sensor,
    a receiver, connected to the one or more antennas, for detecting an amount of electromagnetic radiation provided by the sensor in response to the transmitted electromagnetic radiation, and
    a processor for determining environmentally-induced change to the structure based on a change in the electromagnetic response caused by environmentally-induced changes to the parasitic element.

9. The system in claim 8, wherein the electromagnetic radiation between the sensor and the sensor reader is near field electromagnetic radiation communicated wirelessly.

10. The system in claim 8, wherein the electromagnetic radiation between the sensor and the sensor reader is far field electromagnetic radiation communicated wirelessly, wherein the sensor is configured to reflect back to the sensor reader a modulated version of the transmitted electromagnetic radiation.

11. The system in claim 8, where the inductive element is an antenna.

12. The system in claim 8, wherein the parasitic element is a conductor or dielectric that is in close proximity to but electrically insulated from the inductive element.

13. The system in claim 8, wherein the sensor is attached to a structure and changes to the parasitic element can be correlated to an environmentally-induced change to the structure.

14. The system in claim 8, wherein the environmentally-induced change to the structure includes one or more of the following characteristics: corrosion, erosion, exposure, physical or chemical change, a cumulative damage, or degradation of the structure or a protective coating on the structure.

15. The system in claim 8, further comprising:
a reference element for measurement compensation,
wherein the reader is configured to receive another amount of electromagnetic radiation provided by the reference element in response to the transmitted electromagnetic radiation,
wherein the other amount of radiation is substantially unaffected by the parasitic element, and
wherein the processor is configured to reduce or eliminate one or more environmental factors other than the desired one or more characteristics.

16. The system in claim 15, wherein the processor is configured to differentiate between the inductive element and the reference element based on one or more of the following: resonant frequency of the element, polarization of the element, phase of the element, differences in timing associated with the radiation received from the element, or differences in information modulated onto the radiation received from the element.

17. The system in claim 15, wherein the processor is configured to differentiate between the inductive element and the reference element based on differences in information modulated onto the radiation received from the element.

18. The system in claim 15, wherein the processor is configured to quantify an amplitude of the radiation received from each of the inductive element and the reference element.

* * * * *